(12) United States Patent
Schentag et al.

(10) Patent No.: US 10,349,820 B2
(45) Date of Patent: Jul. 16, 2019

(54) DEVICE AND METHODS FOR IN VIVO MONITORING OF AN INDIVIDUAL

(75) Inventors: Jerome J. Schentag, Eggertsville, NY (US); Frank V. Bright, Williamsville, NY (US); David T. D'Andrea, Getzville, NY (US)

(73) Assignee: TheraSyn Sensors, Inc., Amherst, NY (US)

( * ) Notice: Subject to any disclaimer, the term of this patent is extended or adjusted under 35 U.S.C. 154(b) by 780 days.

(21) Appl. No.: 13/808,463

(22) PCT Filed: Jul. 12, 2011

(86) PCT No.: PCT/US2011/043759
§ 371 (c)(1),
(2), (4) Date: May 17, 2013

(87) PCT Pub. No.: WO2012/024034
PCT Pub. Date: Feb. 23, 2012

(65) Prior Publication Data
US 2013/0225922 A1  Aug. 29, 2013

Related U.S. Application Data

(60) Provisional application No. 61/363,358, filed on Jul. 12, 2010.

(51) Int. Cl.
*A61B 1/00* (2006.01)
*A61B 1/303* (2006.01)
(Continued)

(52) U.S. Cl.
CPC .......... *A61B 1/041* (2013.01); *A61B 1/00186* (2013.01); *A61B 1/043* (2013.01);
(Continued)

(58) Field of Classification Search
CPC . A61B 1/041; A61B 5/14539; A61B 5/14546; A61B 1/00016; A61B 5/14532; A61B 5/0075; A61B 5/145; A61B 1/303
(Continued)

(56) References Cited

U.S. PATENT DOCUMENTS

| 5,279,607 A | 1/1994 | Schentag et al. |
| 5,395,366 A | 3/1995 | D'Andrea et al. |

(Continued)

OTHER PUBLICATIONS

Zhang et al., CN 101288578A, English Machine Translation, dated Oct. 2008, espacenet.com, 13 pages.*

*Primary Examiner* — John P Leubecker
*Assistant Examiner* — Shankar Raj Ghimire
(74) *Attorney, Agent, or Firm* — Hodgson Russ LLP

(57) ABSTRACT

The present invention may be embodied as a retrievable device capable of sensing one or more properties of an individual (e.g., chemical or physical parameters, etc.) In use, the retrievable device can continuously determine the chemical concentrations within the vaginal tract. An embodiment of the retrievable device comprises a first housing having a light source and an image capture device, a second housing removably connected to the first housing and having a sensor, and a fitting for retrieving the device. The sensor may be an analyte sensor configured to obtain at least one measurement of a concentration of an analyte in a fluid. The analyte sensor comprises a sensor substance in a sol-gel material so the sensor substance reversibly interacts with an analyte of interest. In addition, the retrievable device can be configured to determine different physical parameters and re-implanted.

22 Claims, 14 Drawing Sheets

(51) Int. Cl.
*A61B 1/04* (2006.01)
*A61B 1/05* (2006.01)
*A61B 1/06* (2006.01)
*A61B 5/07* (2006.01)
*A61B 5/145* (2006.01)
*A61B 5/00* (2006.01)

(52) U.S. Cl.
CPC ............ *A61B 1/051* (2013.01); *A61B 1/0684* (2013.01); *A61B 1/303* (2013.01); *A61B 5/07* (2013.01); *A61B 5/14507* (2013.01); *A61B 5/14532* (2013.01); *A61B 5/14546* (2013.01); *A61B 5/435* (2013.01)

(58) Field of Classification Search
USPC ........................................................ 600/160
See application file for complete search history.

(56) References Cited

U.S. PATENT DOCUMENTS

| | | |
|---|---|---|
| 5,637,507 A | 6/1997 | Wicks et al. |
| 6,330,464 B1 | 12/2001 | Colvin et al. |
| 6,632,175 B1 | 10/2003 | Marshall |
| 6,709,387 B1 | 3/2004 | Glukhovsky et al. |
| 6,923,768 B2 | 8/2005 | Camus et al. |
| 6,944,316 B2 | 9/2005 | Glukhovsky et al. |
| 7,076,284 B2 | 7/2006 | Segawa et al. |
| 7,181,261 B2 | 2/2007 | Silver et al. |
| 7,473,218 B2 | 1/2009 | Segawa et al. |
| 7,647,090 B1 | 1/2010 | Mordechai |
| 7,865,229 B2 | 1/2011 | Horn |
| 7,938,775 B2 * | 5/2011 | Rabinovitz ............ A61B 1/041 600/101 |
| 2001/0051766 A1 * | 12/2001 | Gazdzinski ........ A61B 1/00016 600/309 |
| 2002/0128542 A1 | 9/2002 | Van Over |
| 2003/0191430 A1 | 10/2003 | D'Andrea et al. |
| 2004/0199054 A1 * | 10/2004 | Wakefield .......... A61B 1/00156 600/160 |
| 2005/0100937 A1 | 5/2005 | Holmes |
| 2005/0154277 A1 | 7/2005 | Tang et al. |
| 2005/0177035 A1 * | 8/2005 | Botvinick .......... A61B 5/14532 600/347 |
| 2005/0228308 A1 | 10/2005 | Iddan et al. |
| 2006/0041193 A1 | 2/2006 | Wright et al. |
| 2006/0206005 A1 * | 9/2006 | Ou-Yang ............. A61B 5/0084 600/160 |
| 2006/0275853 A1 | 12/2006 | Mathew et al. |
| 2008/0063703 A1 | 3/2008 | Gross et al. |
| 2008/0064938 A1 | 3/2008 | Semler et al. |
| 2008/0103440 A1 | 5/2008 | Ferren et al. |
| 2008/0194912 A1 | 8/2008 | Trovato et al. |
| 2008/0200757 A1 | 8/2008 | Glukhovsky et al. |
| 2008/0249360 A1 | 10/2008 | Li et al. |
| 2008/0262313 A1 | 10/2008 | Shimizu et al. |
| 2008/0284599 A1 | 11/2008 | Zdeblick et al. |
| 2008/0287833 A1 | 11/2008 | Semler et al. |
| 2009/0011945 A1 | 1/2009 | Bright et al. |
| 2009/0124874 A1 | 5/2009 | Gono et al. |
| 2009/0137876 A1 | 5/2009 | Brophy |
| 2009/0240107 A1 | 9/2009 | Igarashi et al. |
| 2009/0275923 A1 | 11/2009 | Shimizu et al. |
| 2009/0281395 A1 | 11/2009 | Semler et al. |
| 2009/0306632 A1 | 12/2009 | Trovato et al. |
| 2009/0312627 A1 | 12/2009 | Matott et al. |
| 2010/0033324 A1 | 2/2010 | Shimizu et al. |
| 2010/0045309 A1 | 2/2010 | Zou et al. |
| 2010/0049012 A1 | 2/2010 | Dijksman et al. |
| 2010/0049120 A1 | 2/2010 | Dijksman et al. |
| 2010/0056874 A1 | 3/2010 | Dijksman et al. |
| 2010/0063486 A1 | 3/2010 | Dijksman et al. |
| 2010/0179397 A1 | 7/2010 | Bright et al. |
| 2010/0312483 A1 * | 12/2010 | Peyser .................. G01N 33/52 702/19 |
| 2011/0282144 A1 * | 11/2011 | Gettman ................ A61B 1/041 600/109 |

\* cited by examiner

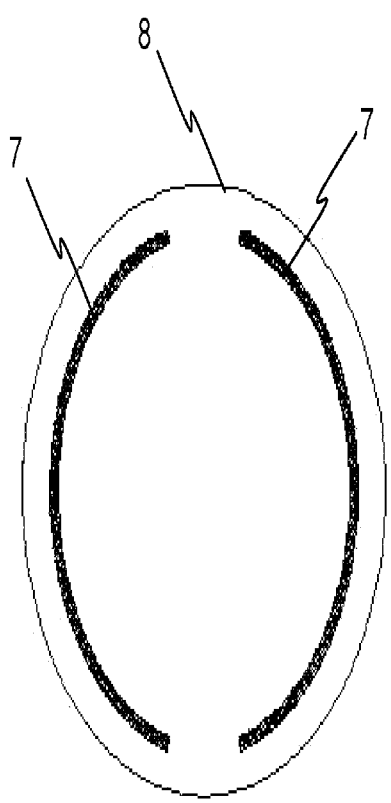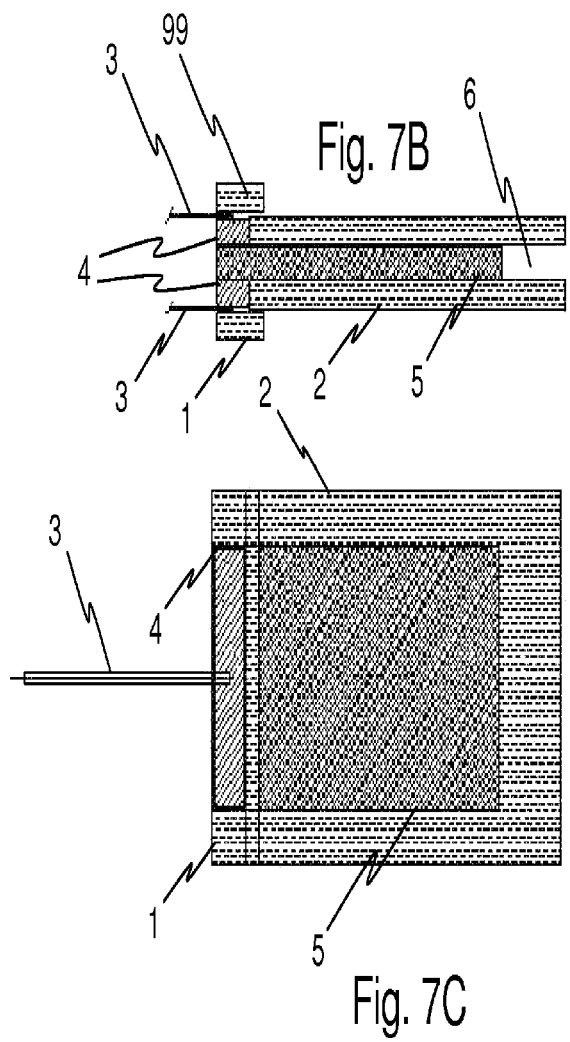

DEVICE AND METHODS FOR IN VIVO MONITORING OF AN INDIVIDUAL

CROSS-REFERENCE TO RELATED APPLICATION

This application claims the benefit of priority to U.S. provisional patent application Ser. No. 61/363,358 filed Jul. 12, 2010, the disclosure of which is incorporated herein by reference.

FIELD OF THE INVENTION

The present invention relates to a device for biological monitoring, and more specifically to a device for, and methods of, in vivo monitoring of an individual.

BACKGROUND OF THE INVENTION

In recent years, ingestible devices containing sensors or cameras have been used by the medical profession as a way to monitor (e.g., measure the properties of, etc.) the alimentary canal of individuals. However, previous devices have not been provided for retrievable implantation in an individual. Additionally, because of the nature of ingestible devices, previous devices have been constructed as capsules that were not reconfigurable (and re-implantable).

Accordingly, there is a need for a retrievable device which will allow for in vivo monitoring of an individual.

BRIEF SUMMARY OF THE INVENTION

A device according to an embodiment of the present invention is configured for retrievable implantation into an individual. The device comprises a first housing having a light source configured to illuminate a region of the environment external to the first housing—a "field-of-view." An image capture device is disposed within the first housing and positioned to capture an image of at least a portion of the field-of-view. The device comprises a second housing configured to be removably connected to the first housing and having a sensor. The device also has a fitting attached to the first housing, the second housing, or both. The sensor may be electrically connected to the image capture device. The sensor may also comprise a detector configured to detect electromagnetic energy emitted by the sensor substance.

The sensor may be an analyte sensor capable of measuring the concentration of an analyte in a bodily fluid present at the implantation site. Such an analyte sensor may comprise a sensor substance in a sol-gel material. The sensor substance will emit electromagnetic energy when in contact with the analyte of interest and electromagnetic excitation energy is received by the sensor substance. Multiple sensor substances may be used. The multiple sensor substances may be the same sensor substance, different sensor substances, or a combination of similar and different substances. For example, an array may be formed from a plurality of sensor substances, each configured to respond to a different analyte of interest.

In another embodiment of a sensor according to the present invention, the sensor comprises a sensor substance in the form of an antibody bonded to a reporter molecule. The antibody is configured to interact with an analyte of interest. The reporter molecule is configured to respond to interaction with an analyte by emitting electromagnetic energy (either independently or in the presence of excitation energy).

The sensor may be a parametric sensor for measuring a physical parameter of the environment external to the housing. For example, the physical parameter may be sound, pH, temperature, pressure, or otherwise. The device may further comprise a 3-axis accelerometer. In another embodiment, the sensor may be a 3-axis accelerometer.

The device may further comprise a transmitter, receiver, or both (separately or in the form of a transceiver) for communication with external devices.

The device may further comprise an electronic storage device, for example, a memory device.

The invention may also be embodied as a method of monitoring an individual. The monitoring may utilize a retrievable device for in vivo monitoring of the individual. The device may be similar to the device described herein. The method comprises the steps of implanting the retrievable device in the individual, using the retrievable device to make at least one measurement of a first property of the individual, and using the fitting of the retrievable device to extract the retrievable device from the implantation site of the individual.

The method may further comprise the step of configuring the retrievable device to make at least one measurement of a second property of the individual. The retrievable device configured for a measurement of a second property is re-implanted in the individual. And, the retrievable device is used to make at least one measurement of a second property of the individual.

DESCRIPTION OF THE DRAWINGS

For a fuller understanding of the nature and objects of the invention, reference should be made to the following detailed description taken in conjunction with the accompanying drawings, in which:

FIG. 7A is a cross-sectional view of a second housing according to an embodiment of the present invention showing a piezoelectric pressure sensor configuration;

FIG. 7B is a side view of a piezoelectric sensor component;

FIG. 7C is a top view of the piezoelectric sensor component of FIG. 7B;

DETAILED DESCRIPTION OF THE INVENTION

Figure 14:
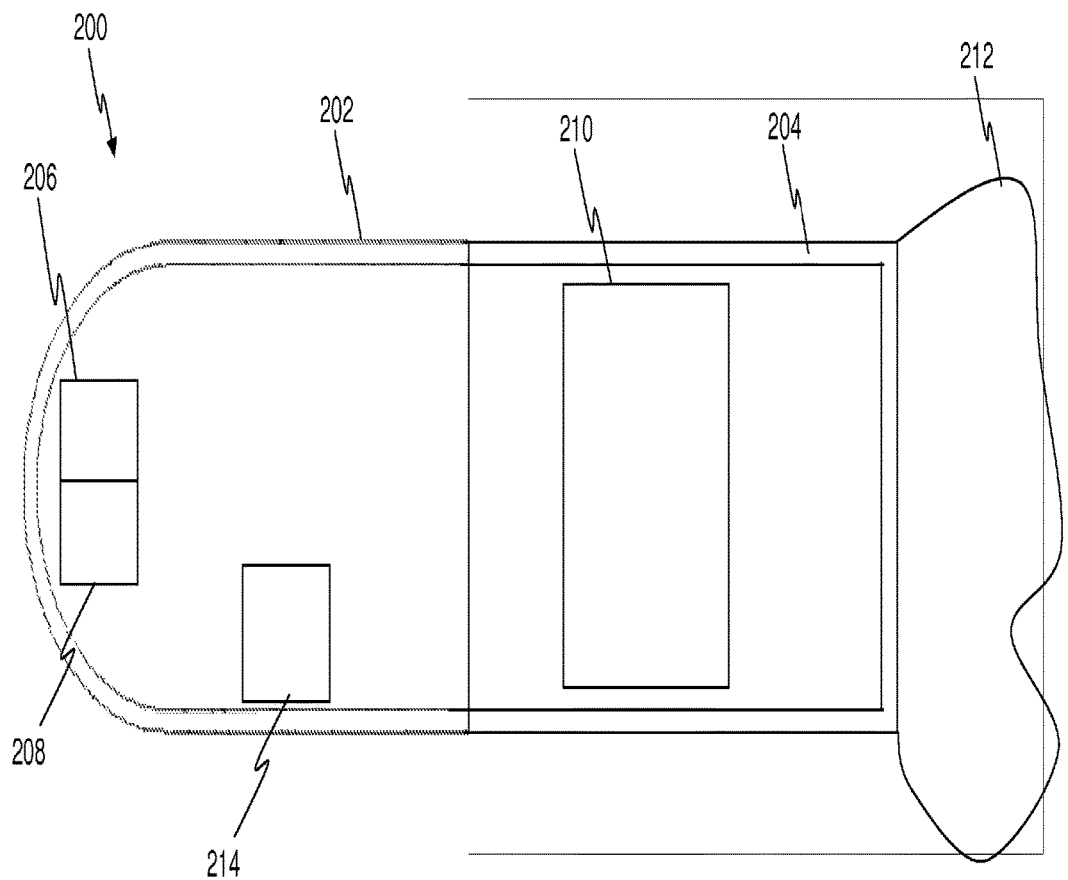
FIG. 14 depicts a device according to an embodiment of the present invention.

A device 200 according to an embodiment of the present invention, depicted in FIG. 14, is configured for retrievable implantation into an individual. It should be noted that the terms "implanted" or "inserted" are used interchangeably throughout this disclosure and should be broadly interpreted as placing the device into an individual. Implantation into an individual allows the device 200 to perform "in vivo" monitoring (e.g., measure a parameter, etc.) of an individual. In an embodiment, the device 200 may be configured to be implanted into a body orifice of the individual. For example, where the individual is a mammal, the device 200 may be configured to be implanted in the mouth, the anus, the vagina, etc. The device 200 may be sized, shaped, and/or otherwise configured differently depending on the intended implantation site. For example, a device 200 according to an embodiment of the present invention may be capsule shaped.

The device comprises a first housing 202 having a light source 206. The light source 13 is configured to illuminate a region of the environment external to the first housing 202—a "field-of-view." The light source 206 may be a light-emitting diode ("LED"). The light source 206 may be located within the first housing 202 such that the first housing 202 protects the light source 206 from fouling by any bodily fluids that may be present in the implantation site. In such embodiments, the first housing 202, or at least a portion of the first housing 202, may be transmissive so that the light from the light source 206 can pass through the first housing 202. The light source 206 may be configured to illuminate a field-of-view at the leading end of the device 200 (when the device 200 is configured to have ends—e.g., a capsule shape, etc.) Alternatively, the light source 206 may be configured to illuminate a field-of-view at a trailing end of the device 200, or a field-a-view at a side of the device 200. The field-of-view may be wide or narrow as suited to the purpose of the device 200. The illumination may be of any brightness and color temperature as suited to the purpose of the device 200.

The device 200 also includes an image capture device 208 disposed within the first housing 202. The image capture device 208 may be, for example, a still camera, a video camera, or a camera capable of both still image capture and video capture. The image device 208 may be, for example, capable of capturing three-dimensional image information. For example, the image capture device 208 may comprise multiple image sensors spaced apart from each other at a fixed distance. In this way, each image sensor will capture a view of the scene from a different perspective, and the perspective images can be merged to provide three-dimensional image data. The image capture device 208 may be, for example, an infrared camera and/or a visible light camera.

The image capture device 208 is positioned to capture an image (or multiple images) of at least a portion of the field-of-view. At least a portion of the first housing 202 is transmissive in order to allow light to pass through to the image capture device 208. For example, at least a portion of the first housing 202 may be clear (i.e., transparent). In an embodiment, a portion of the first housing 202 may be shaped in order to act as a lens for the image capture device 208. The lens may be configured to show a magnified view, a wide-angle view, or otherwise. In certain cases, the lens may distort the optical view of the image capture device, for example, the lens may be a so-called "fish-eye" lens capable of a wide field-of-view, but distorting the image. A portion of the first housing may be configured to act as a filter in order to filter certain wavelengths of light from reaching the image capture device 208.

The device 200 further comprises a second housing 204 configured to be removably connected to the first housing 202. For example, the second housing 204 and first housing 202 may screw to one another, clip to one another, or otherwise attach in a removable fashion. Such removable connection allows a device 200 according to the present invention to be flexibly configured with additional modules (further detailed below) and/or reconfigured to include different first or second housings with different components within.

The second housing 204 of the device 200 further comprises a sensor 210. The sensor 210 may be configured for monitoring (e.g., measuring, etc.) a parameter of the individual. Various embodiments of the sensor 210 are further described below.

The device 200 further comprises a fitting 212 attached to the first housing 202, the second housing 204, or both. The fitting 212 is used to retrieve the device 200 from the implantation site. The fitting 212 can be an orifice for snagging the device 200 with a hook or similar tool, a threaded orifice for securing a threaded tool, a string, a rod, or any appendage for grasping the device 200, site for use of a tool for retrieving the device 200, or other configuration to aid in the retrieval of the device 200.

In an embodiment of a device 200 according to the present invention, the sensor 210 is electrically connected to the image capture device 208. In this manner, the sensor is able to generate a signal for controlling the operation of the image capture device 208.

The sensor of a device according to the present invention may be an analyte sensor capable of measuring the concentration of an analyte in a bodily fluid present at the implantation site. For example, the analyte sensor may be capable of measuring relatively small molecules (e.g., glucose, etc.) or relatively large molecules (e.g., proteins—hemoglobin, etc.) The capability, function, and structure of such analyte sensors is described in further detail infra. An embodiment of an analyte sensor is configured to obtain at least one of measurement of the concentration of an analyte in the bodily fluid. The analyte sensor may be configured to obtain a plurality of measurements. The analyte sensor may be configured to make continuous measurements. In an embodiment 44 of an analyte sensor depicted in FIG. 6, the analyte sensor 37 comprises a sensor substance 50 in a sol-gel material. Sol-gel materials include materials derived from a sol-gel process. The sensor substance 50 is configured to reversibly interact with an analyte of interest. The sensor substance 50 may be able to sample an analyte at a rate of approximately one second or less, depending on the analyte and configuration of the analyte sensor 37. The sampling rate may be higher for larger molecules, or lower for smaller molecules. In addition, the analyte sensor itself may be disposed within the housing or external to the housing.

When the sensor substance 50 is in contact with the analyte of interest and electromagnetic excitation energy is received by the sensor substance 50, the sensor substance will emit electromagnetic energy. For example, the sensor substance 50 may be exposed to electromagnetic excitation energy in the form of light energy. Such a sensor substance 50 is also configured to react to a specific analyte of interest (e.g., glucose, etc.). When such a sensor substance 50 is exposed to the analyte of interest and the excitation energy, the sensor substance 50 will emit energy, for example the sensor substance 50 may fluoresce. Other forms of electromagnetic excitation energy (e.g., infrared, ultraviolet, etc.) can by used. The sensor substance 50 can be configured to emit energy in different ways and in different forms. For example, the sensor substance 50 can be configured to emit modulated light energy, or energy of specific wavelengths, or otherwise.

Multiple sensor substances may be used. For example, an array may be formed from a plurality of sensor substances, each configured to respond to a different analyte of interest. In this way, multiple chemical parameters (i.e., concentrations of multiple analytes) may be measured simultaneously.

The sensor substance 50 of a device 200 according to an embodiment of the present invention is configured to be in contact with the bodily fluid. In an embodiment, the sensor substance 50 may be located within the external bounds of the second housing 204. In such an embodiment, portions of the second housing 204 may include one or more apertures 52 through which bodily fluid may move to contact the sensor substance 50. A cover material, such as, but not limited to, a membrane 45 or a mesh, may cover the apertures 52 and allow the bodily fluid to pass through. In another embodiment, the sensor substance 50 is located on the second housing such that the sensor substance 50 is exposed to the bodily fluid without the solid particles of the respective fluid passing into the device 200.

In an embodiment of the present invention, the analyte sensor 44 is configured to generate a signal for controlling the device 200. For example, the analyte sensor 44 may be configured to generate a signal to the image capture device 208, such that the image capture device 208 will capture an image. In another example, the analyte sensor 44 may be configured to detect hemoglobin and trigger the image capture device 208 to capture a plurality of images. Such an embodiment is useful for detecting and photographing portions of the individual which may be bleeding. Other sensor configurations are possible and within the scope of the present invention.

The analyte sensor 44 of embodiments of a device 200 of the present invention may also be configured to continuously measure a concentration of analyte in the bodily fluid. In an embodiment, the analyte sensor 44 is configured to be reversible. The term "reversible" or "reversibility" as used herein refers to the ability of the analyte sensor 44 to detect the presence of an analyte within a sample in a continuous manner as the sample concentration within the sample increases and decreases and to do so in an unbiased manner. The presence of the analyte is identified by detecting a signal that is indicative of the analyte concentration. The absence of the analyte can be identified by a lack of a detectable signal or a signal that is not significantly different than the background signal. Upon re-exposure to the analyte the signal can again be recorded. Any change over time in the concentration of the analyte in the immediate environment of the sensor results in a signal from the sensor that is readily correlated to the analyte concentration in the sample at the point in time of the signal measurement. The signal is also an accurate and precise measure of the analyte concentration at that specific point in time. The reversible nature of the interaction between the sensor and the analyte allows detection of an analyte in a continuous manner and no change in temperature or pressure or other means (e.g., pH swing, chaotrope, denaturant, etc.) is required to disengage/dissociate the analyte from the sensor. We have successfully used the present method for reversibly and continuously detecting analytes over a period of several months. For example, the signal from the chemical sensor was continuously detected over a period of at least 30 days with minimal drift (relative standard deviation ≤5%). The reversible nature of the analyte sensor 44 can be performed through physical or chemical means. For example, an optical fiber brush may be employed to clear the active surface of the analyte sensor between measurements. In another example, the analyte sensor 44 can be configured to detect the analyte as it flows through the sensor.

In another embodiment of a sensor according to the present invention, the sensor comprises a sensor substance in the form of an antibody bonded to an optically active (e.g., fluorescent, etc.) reporter molecule. The antibody is configured to interact with an analyte of interest. The reporter molecule is configured to respond to interaction with an analyte by emitting electromagnetic energy (either independently or in the presence of excitation energy). The analyte may be captured by the sensor for analysis (e.g., ELISA assay, etc.).

The sensor may also comprise a detector 17 configured to detect electromagnetic energy emitted by the sensor substance 50 (see, e.g., FIG. 4B). For example, in sensors having fluorescent or otherwise luminescent reporting capabilities (e.g., the aforementioned sol-gel based and antibody based methods, or others), a detector 17 may be used to sense the energy emitted by such activity. In an embodiment, the detector 17 is a CMOS detector that monitors the emitted energy. In another embodiment, the detector 17 is an array of CMOS detectors. Configuring CMOS detectors to react to certain wavelengths of light is well-known in the art. In an embodiment, the detector 17 is a photodiode. The device 200 may also comprise a controller 34 in electronic communication with the detector 17 for measuring a concentration of analyte based on the detected electromagnetic energy. The controller 34 may compare the detected electromagnetic energy with a known value, or may calculate analyte concentration based on an algorithm specific to the known electromagnetic response.

The sensor substance 50 may require electromagnetic excitation energy in order to respond when in the presence of an analyte. In an embodiment, electromagnetic excitation energy is provided to the sensor substance 50 by the light source 13 of the first housing. If additional light sources are employed, these light sources may also provide the required electromagnetic excitation energy. The sensor substance 50 may receive the energy through ambient radiation, or the energy may be directed as, for example, a light channel through a fiber-optic cable. In another embodiment, the analyte sensor 37 further comprises an electromagnetic excitation energy source 13 configured to provide electromagnetic excitation energy to the sensor substance 50. For example, the energy source 13 may be a driving LED configured to emit a specific wavelength, or wavelength range of light. The driving LED may also produce a modulated signal to aid in the computation of analyte concentration.

The sensor 210 may be a parametric sensor for measuring a physical parameter of the environment external to the housing. For example, the physical parameter may be sound, pH, temperature, pressure, movement (3-axis accelerometer), or otherwise. The parametric sensor may include diodes, capacitive pressure sensors, and microphones. Other parametric sensors as known in the prior art could be adapted for use in the device. The parametric sensor may comprise a piezoelectric material configured to measure pressure.

A device according to an embodiment of the present invention, depicted in FIGS. 4A and 4B, may further comprise a first housing sensor 38 disposed in the first housing 1. The first housing sensor 38 may be of any type, such as those described above.

Figure 15:
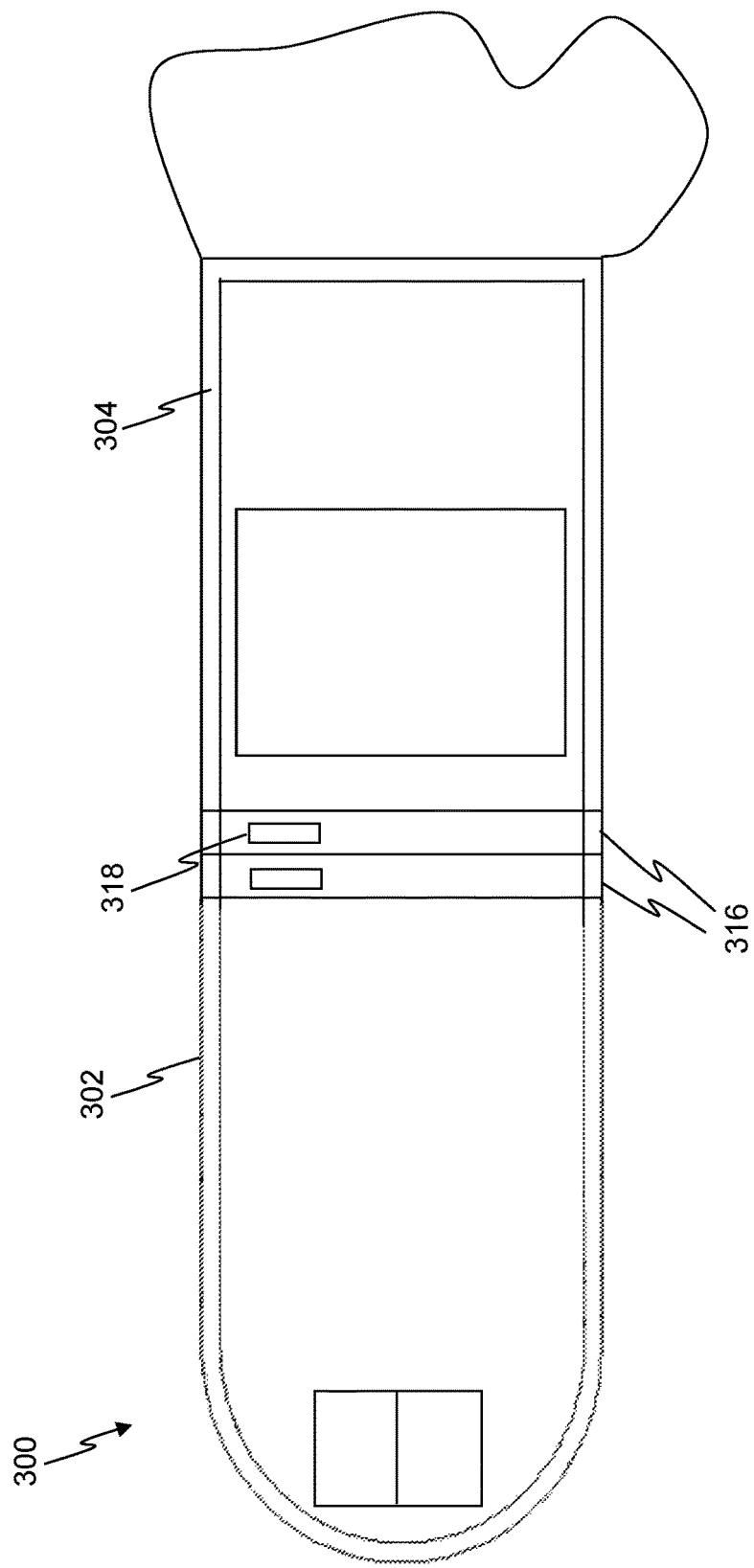
FIG. 15 depicts a device according to an embodiment of the present invention having sensor modules.

A device 300 according to an embodiment of the present invention, depicted in FIG. 15, may comprise one or more sensor modules 316. Each sensor module 316 is configured to be removably connected between the first housing 302 and the second housing 304. Each sensor module 316 has at least one sensor 318 disposed within. In this way, a device 300 according to embodiments of the present invention may be configured with one or more sensor modules 316 with the same or different sensors 318 selected according to the needs of the individual. The device 300 may also be retrieved, reconfigured, and re-implanted as the needs of the individual change or are better understood. For example, a device may be implanted to detect temperature (via the sensor) and monitor through pictures. If the temperature rises above a determined threshold, the device can be retrieved and reconfigured to have a sensor module capable of detecting an infection. For example, a sensor of the sensor module may have an analyte sensor. The reconfigured device may then be reimplanted in the individual.

In an embodiment, the device may further comprise a 3-axis accelerometer 32. In another embodiment, the sensor may be a 3-axis accelerometer 32. By way of examples, this would record patient activity such as cramping during pregnancy which might indicate premature delivery or daily energy monitoring for assistance with the treatment of diabetes.

The device 101 may further comprise a transmitter, receiver, or both (separately or in the form of a transceiver). The transmitter and/or receiver may be in electronic communication with the image capture device, the sensor, or both. In an embodiment, a transceiver is used configured to transmit collected data to an external device. For example, the transceiver may transmit data from the sensor, the image capture device, or both to a console monitored by an operator. The transceiver may also accept commands for control of the device's systems. It should be noted that the terms "transceiver" and "transmitter and/or receiver" are used interchangeably throughout this disclosure, and should be given the broadest interpretation as at least any device configured to transmit and/or receive information. In an example, the transceiver may send data to an operator's console, where an operator may detect a condition where an image should be captured by the image capture device. Other functions will follow from the inclusion of a transceiver in a device.

The device 200 may further comprise an electronic storage device 214, for example, a memory device. The electronic storage device 214 may store data from the sensor 210 and/or the image capture device 208 for later retrieval of such data.

The invention may also be embodied as a method 100 of monitoring an individual. The monitoring may utilize a device as previously described for retrievable implantation for in vivo monitoring of the individual. The method 100 comprises providing 103 a retrievable device. The device may be of any embodiment described herein where the device comprises a first housing having a light source for illuminating a field-of-view. The first housing of the device also has an image capture device positioned to capture an image of at least a portion of the field-of-view. The device further comprises a second housing with a sensor. The second housing is configured to be removably connected to the first housing. The device further comprises a fitting for retrieving the device.

The method 100 comprises the step of implanting 106 the retrievable device in the individual. As stated above, implantation (insertion) may be implantation in a body orifice, for example (in a mammal) the mouth, the rectum, the vagina, or otherwise. The retrievable device is used 109 to make at least one measurement of a first property of the individual. For example, the sensor of the device may be an analyte sensor, and the analyte sensor may be used to measure the concentration of an analyte in a bodily fluid of the individual. In another example, the sensor may be a parametric sensor for measuring a physical parameter, such as without limitation, temperature, pressure, sound, or pH. The sensor may make continuous measurement of the property of the individual. The fitting of the retrievable device is used 112 to extract the retrievable device from the implantation site of the individual.

The method 100 may comprise the step of using 115 the image capture device to capture at least one image of a portion of the individual. The portion of the individual is proximate to the retrievable device. For example, in the case where the retrievable device is inserted into the vagina of an individual, the image capture device may be used to capture images (including still, video, 3D, etc.) of the cervix of the individual. The sensor and the image capture device may be electrically connected, and the method 100 may comprise the step of controlling 118 the operation of the image capture device with a trigger signal generated based on the at least one measurement. For example, in the above example where the retrievable device is inserted in the vagina of an individual, the sensor may be able to measure movement or pressure (for example, caused by a contraction during labor) and generate a signal to the image capture device to capture an image of the cervix. In this way, a medical professional may monitor the dilation of the cervix of an individual during labor.

The retrievable device may have a transmitter and/or a receiver. The transmitter may be configured to transmit 121 signals received from the sensor and/or image capture device. For example, the value of a measurement made by the sensor may be transmitted to an external device for monitoring by an operator. Similarly, in another example, images captured by the image capture device may be transmitted by the transmitter to an external device. The receiver may be configured to receive signals from an external device (e.g., a remote transmitter, etc.) In this way, an operator using an external device may trigger the image capture device to capture an image and/or the sensor to take at least one measurement.

The method 100 may further comprise the step of configuring 124 the retrievable device to make at least one measurement of a second property of the individual. For example, the second housing (and sensor) may be disconnected from the first housing and the second housing may be exchanged for an alternate second housing with a different sensor (and reconnected to the first housing). In another example, the second housing may be disconnected from the first and the sensor within the second housing exchanged for an alternate sensor. In another example, one or more sensor modules each having at least one sensor may be connected between the first housing and the second housing. In this way the retrievable device may be reconfigured in any of various ways to take a measurement of a second property (or several properties).

The retrievable device configured for a measurement of a second property is re-implanted 127 in the individual. And, the retrievable device is used 130 to make at least one measurement of a second property of the individual.

Additional exemplary embodiments of the above-described device and method are provided below.

A capsule for vaginal use may be small enough to be easily inserted, functional over days of continuous use, and biologically inert. The transmission signal is strong enough to be received by a remote receiver, and the receiver may be small enough to be carried by the individual. In an embodiment a remote receiver is a mobile phone or handheld computer device with storage and communication features. Each capsule may transit or receive data using one of 256 available digital transmission channels to reduce interference from other transmission sources (or other capsules) in the near vicinity. The capsule transmitter operating in conjunction with the capsule receiver and an external capsule receiver may incorporate an adaptive transmitter power level control algorithm. Transmitted power may automatically be adjusted to create the lowest data error rate. This approach reduces the power consumption of the capsule by limiting the transmitted power level to the lowest value required to produce a low error rate transmission.

The present invention broadly provides for a practical vaginally inserted capsule that is arranged to sense one or more chemical and/or physiological parameters within a individual, and to transmit such parameters to an extracorporeal receiver. In use, the capsule and receiver perform the method of continuously determining the chemical concentrations and physiological measurements within a vaginal tract of a mammal. These measurements allow remote visual monitoring of the cervical opening during pregnancy. During the time that vaginal anatomy is under video monitoring, there is additional advantage gained by the continuous sensing of chemicals and proteins (see U.S. Pat. Nos. 6,241,948 and 6,589,438) in the fluids of the vaginal canal of a mammal. This highlighted section is the good stuff on the combination of the technologies. Previous embodiments of capsules have not been able to provide data regarding physical activity of the patient or quantify the magnitude, duration and frequency of contractions occurring in late pregnancy. By incorporating two piezoelectric foil based compressive force (pressure) sensors covering 60% of the capsules outer shell circumference and the incorporation of a three axis accelerometer within the capsule, data can be collected regarding patient physical activity and contractions. The capsule can monitor the heartbeat of the mother and fetus. The capsule also contains a high resolution, fast response temperature sensor used to monitor patient vaginal temperature and assist with calibration of chemical and physical sensors to insure high accuracy measurements. Vaginal temperature is helpful in monitoring infection or the hormonal cycles of the mammal to assess fertility.

An embodiment of a method includes the steps of inserting and wearing the vaginal capsule, the vaginal capsule having one or more sensors for chemical and physical characteristics; transmitting a signal from the capsule; receiving the transmitted signal; determining the real-time concentrations of substances in the fluid of the vagina of a mammal; and determining the real-time physical properties of the vaginal canal and cervical opening as a function of the received signal(s). The received digital photograph signal also indicates the visual status at the time of chemical and physical measurements of one or more sensed parameters. The capsule may contain a receiver that provides for external or internal (pre-programmed) sample-on-demand functions that may be initiated by sensed parameter pre-set thresholds or initiated by a clinician examining the transmitted data from the capsule in real time. Additionally, data captured by the capsule may transmitted to a Personal Computer (PC) or to a patient worn device such as a wristwatch containing a transceiver and display or a smart phone with a Bluetooth™ application for monitoring the capsule.

The capsule can be powered by small primary or secondary (rechargeable) type batteries. The invention incorporates an activation system for either type of battery chemistry, calibration and recharging system that provides a device that can be used for a month or longer in the same individual. The materials used for the vaginal pills outer shell will be chosen to allow the use of FDA approved cleaning solvents between uses within the same patient.

An embodiment for this device would not include the chemical sensing system and its associated detector. This embodiment would yield a device capable of measuring patient activity, heartbeats from mother and fetus, vaginal contractions and visual observations of dilation of the cervix. For this embodiment the sample-on-demand functions that may be initiated by the start of a contraction as sensed by the accelerometer, heart rate, temperature and pressure sensors.

An embodiment for this device would not include the chemical sensing system and its associated detector. This embodiment would include the camera, the accelerometer, and the acoustic and piezo pressure detector. This embodiment would yield a device capable of measuring patient activity, heart rate of mother and fetus, frequency and duration of contractions, and provide photographic images of dilation of the cervix. For this embodiment the sample-on-demand functions that may be initiated by the start of a contraction as sensed by the accelerometer and temperature sensors.

In an embodiment, a chemistry sensor device is included with a battery and transmitter-receiver and used to monitor glucose concentrations in vaginal fluid in a diabetic patient in need thereof.

Figure 1:
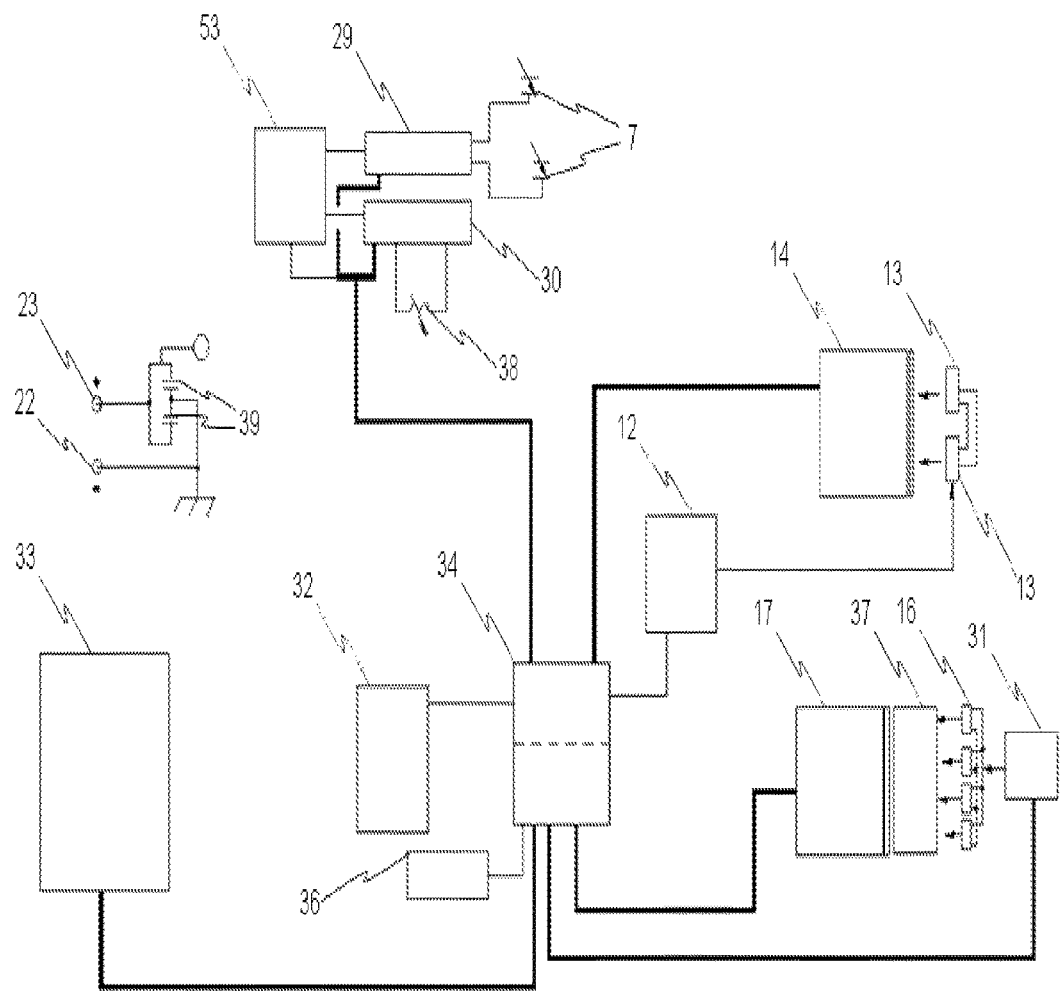
FIG. 1 is a block diagram of the systems of a device according to an embodiment of the present invention.
Figure 2:
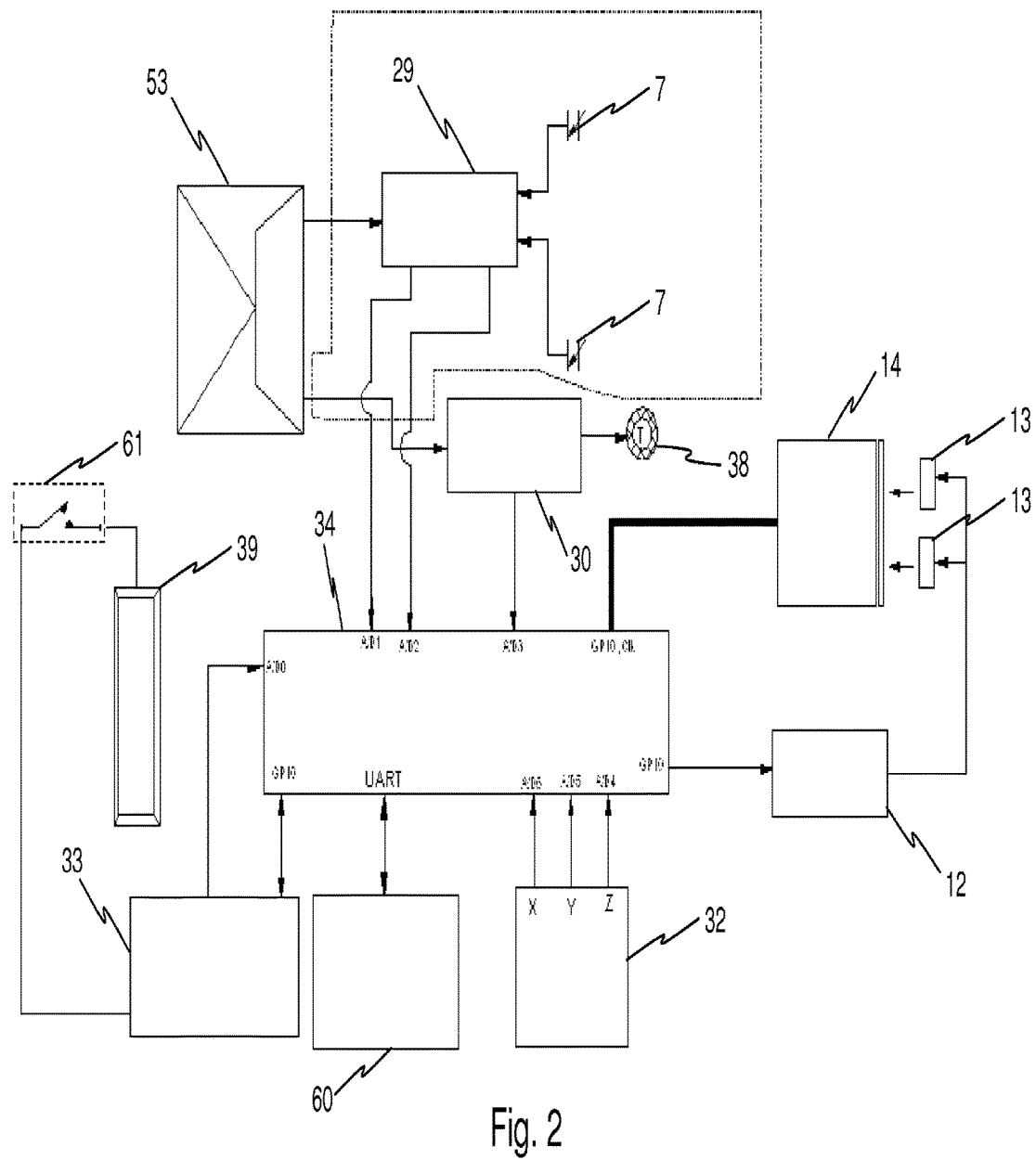
FIG. 2 is a block diagram of the systems of a first housing according to an embodiment of the present invention.
Figure 3:
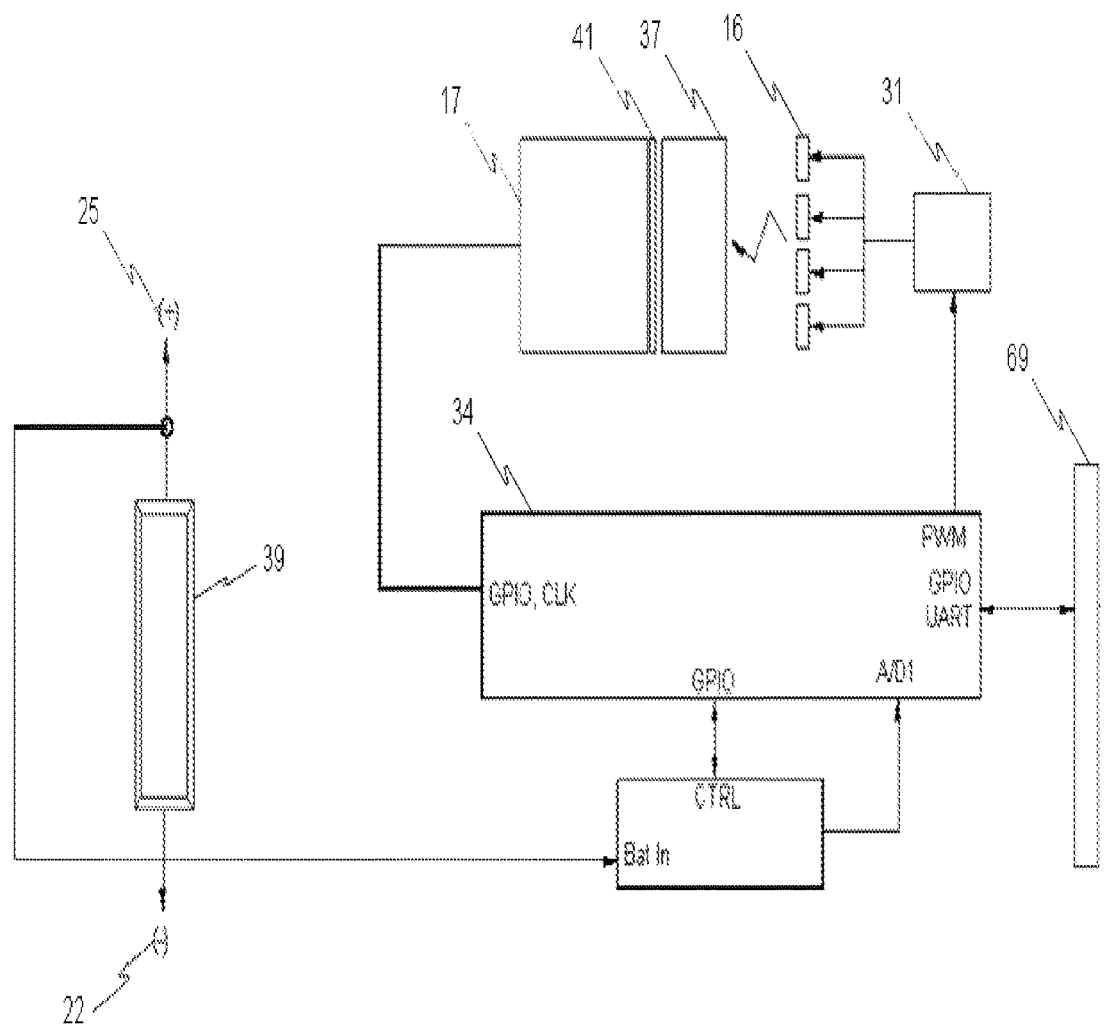
FIG. 3 is a block diagram of the systems of a second housing according to an embodiment of the present invention.

FIGS. 1, 2, and 3 illustrate the main electronic components and their electrical interconnections as a generalized functional block diagram for several embodiments of the present invention. Discrete components supporting each of the major function blocks are not illustrated in these figures. FIG. 1 illustrates components used to produce a single device which embodies the present invention. FIG. 2 illustrates an embodiment of the invention using components suited for a low cost disposable device that also supports remote healthcare provider examination and monitoring of vaginal and cervical status in a pregnant woman. FIG. 3 illustrates the components in an embodiment with a modular chemical sensing system thereby expanding the functionality of the embodiment illustrated in FIG. 2.

The electronic components used within the present invention may include an image capture device 14. For example the image capture device 14 may be a small (2 mm×2 mm) CMOS, video-capable, color camera. The camera may have excellent low light sensitivity. The camera may be mounted at the front (first inserted) end of the device. Camera activity may be event driven to reduce power consumption and to insure that large amounts of image data does not have to be reviewed to find an area of interest. The image can be displayed on a cell phone screen or monitoring device, allowing adjustment of capsule positioning by the patient or by a medical person working with the patient. The image may be transmitted from the cell phone for further processing. A clinician monitoring the data outputs can activate the camera. In addition, the capsule's internal program may activate a camera if a sensed data parameter exceeds a preprogrammed threshold. The CMOS camera is capable of operation in both still frame and continuous video modes.

An example of still frame (single image) operation may include when the accelerometer shows a close frequency of contractions and motions which may be indicative of a patient going into labor. This event or series of events can activate the camera functions of the device in order to determine the status of the cervical opening. A continuous video mode may prove useful to observe contraction activity, monitor the size of the cervical opening, check for abnormal discharges from the cervix, or directly observe conditions such as bleeding or discharge due to infection. In an embodiment, the images and the accelerometer may independently track data, for example monitoring physical activity on the accelerometer side, while monitoring cervical or vaginal canal functionality on the image side. This embodiment is designed to be worn for short periods of time and capture real-time images. In most, but not all embodiments, the device is inserted so that the camera is forward. A recovery fitting can be placed on the opposite end of the device by use of a removable end cap.

It should also be noted that the removable end cap 63 may be an attachment point for the disposable laboratory module component of the vaginal capsule. This module can perform laboratory analyses for many conditions. One configuration of the laboratory module is to define conditions under which the camera module would be activated to capture images. One example includes the detection of an infection, bleeding, or cancers by means of biomarkers, and then issuing a command to image the cervical opening in cases where the source of bleeding, infection, or cancer can be determined by visual inspection of the video signal or still frame photograph. The images and video from image capture device 14 may be passed to a buffer memory (not illustrated) for storage until a data transfer is requested by an external monitoring device.

The laboratory module can function independently of the camera module and would ordinarily function separately if the goal were to monitor chemical conditions such as glucose in a diabetes patient, or in another embodiment, vaginal fluid biomarkers beneficial in the detection of fertility or in a hormone replacement program, or monitoring of chemical conditions such as biomarkers of organ function, metabolic functions or disease detection or diagnosis. Each of the biomarkers could be measured a single time, or continuously over the battery life of the capsule module.

While each module can function independently from the other to perform its functions, an embodiment would involve a connected first housing 1 and second housing 2. The combined components would include the short duration features of a disposable laboratory module, and these functions interact in a data driven directive to the imaging module to take pictures or movies in defined conditions, such as impending delivery or onset of infection.

In an embodiment, one or more light sources 13, for example, Light Emitting Diodes (LEDs), can be arranged in a directional manner to provide adequate illumination. The LEDs may be any color including white. The LEDs can operate in a high-power, pulsed flash mode for single frame camera operation, or a burst illumination mode for video recording. The microprocessor 34, the light circuit 12, and the power switch 33 may control the operational mode and synchronization of the LEDs to the camera. The light circuit 12 may provide either a high-power, short duration pulse to flash the light sources 13 in the camera still frame mode, or continuous lower power short duration pulses synchronized to the camera's frame rate for camera operation in continuous video mode. The camera LED synchronization, mode, image storage and trigger can be controlled by the microprocessor 34.

In the laboratory module, chemical sensing of analytes contained within the fluid may accomplished in an embodiment by a system comprising a LED driver 31, Sensor LEDs 16, sensor cell 37, and sensing array 17—all controlled by a microprocessor 34. Microprocessor 34 can initiate taking a sample at a preprogrammed sampling rate or by an external trigger. The sampling rate can also be modified due to a previous sensed parameter threshold-crossing event. The LED driver 31 can be activated at each sampling interval thereby illuminating a plurality of sensors LEDs 16, which provide optical radiation to and are, focused on the input side of the sensor cell 37. For example there may be between 4 to 6 sensor LEDs 16. In an embodiment, sensor cell 37 is filled with normal saline (0.91% w/v of NaCl) combined with suitable osmotically active, large molecules as to affect no net loss of fluid inside the capsule when it is inside a mammal. The capsule may also contain an active xerogel-based, analyte-responsive site or sites. Each xerogel site can be formulated to respond by a change in its spectroscopic signature (e.g., electronic absorbance, polarization, photoemission of fluorescence, phosphorescence or chemical luminescence, and/or Raman spectroscopy, etc.) to a specific analyte. The sensor cell 37 may have multiple chemical sensing sites contained within the cell. Fluid communication between the xerogel sensor sites and the environmental fluids may be accomplished by wrapping the outer circumference of the cell with a semi-permeable membrane. Fluids and dissolved chemical substances are allowed to equilibrate between the fluid in the capsule and the fluid in the environment. After equilibration across the semi-permeable membrane, the concentration at the sensor site will be the same as the concentration in the environmental fluid. A spectroscopic filter can be located below the xerogel sensing composites to reduce the transmission of electromagnetic radiation not in the frequency band of the desired spectroscopic signal (absorbance, emission, polarization, scattering) from the xerogel sensing sites. The sensing array 17, for example a high resolution Complementary Metal Oxide Semiconductor (CMOS) detector array, can monitor the optical radiation from the plurality of xerogel sites and detect an active site. The level of activation may be passed to microprocessor 34 as an analog value, which can be digitized, stored, reported as a concentration with respect to time and may be further processed to determine if event initiation is warranted.

In an embodiment, the first housing 1 contains a 3-axis accelerometer 32 to measure the magnitude, frequency, acceleration and direction of patient movement. Data from this device can provide detailed information on patient daily physical activity. Accelerometer data may also be used in conjunction with the data from the capsule pressure sensors in first housing 1 to analyze and monitor contractions in the later months of pregnancy. Accelerometer data may also be used in conjunction with the data from the capsule pressure sensors to analyze and monitor contractions. Here, contractions are notable as "cramps" in the later menstrual cycle and analysis of these signals can be used to monitor the effects of medications given to ease the pain and discomfort. Digitization, processing of digitized data, data storage, and measurement interval for the accelerometer may be controlled by a microprocessor 34. In an embodiment of the present invention, the laboratory module may be changed periodically and as needed to provide continuous monitoring of chemical and biomarker data from the patient.

To monitor contractions as an indication of impending birth in the later months of pregnancy, an embodiment of the present invention as shown in FIG. 2 incorporates two piezoelectric polymer foil pressure sensors 7, two Junction Field effect (JFET) operational amplifiers 29, that provide filtering and noise reduction of the sensors output voltage, a high resolution voltage reference 53 to drive the amplifiers, a power switch 33, a thermistor 38, and scaling circuit 30 to measure patient temperature in order to compensate in calculating the values read by the pressure and other sensors. Both the piezoelectric sensors and thermistor can be located within the capsule near the outer surface. The capsule shell may be composed of a semi-rigid plastic or low durometer, FDA approved encapsulant. These, and other materials, can transmit the force of contractions to the pressure sensors. Positioning the thermistor near the outer shell surface of the pill reduces the thermal lag time between the environmental tissue and the sensor, thereby enabling faster sensor response to temperature changes of the tissue.

Microprocessor 34 may control the function of the first housing 1 and second housing 2 including data storage, data transmission, command reception, both internal camera control and remote camera control, CMOS sensor array operation, accelerometer operation, pressure sensor sampling and temperature measurement, and sensor compensation and calibration. Battery power conservation may also be controlled by the microprocessor 34 by offering a variety of low power operation modes that can be used between active measurement and transmission periods. Power to each function module can be controlled by the microprocessor 34 through power switch 33 by turning off each system once it has completed its task. In this manner the average power consumption of the capsule is minimized. The integrated circuit containing the microprocessor may also contain a full duplex software radio transceiver 60 that is 802.11a compliant and capable of transmitting collected data and video once the microprocessor data memory is full. The microprocessor may also accept external commands for control of the capsule's sub systems from an external monitoring device such as a cell phone. In an embodiment, an antenna 36 is provided. It may comprise a fractional wavelength ceramic chip type antenna. Antenna performance and design can be modeled as an assembly including the proximity battery outer shell to optimize RF performance. The radio can be implemented using a series of programmable registers which allows software tuning of performance and offers 256 transmission/reception digital channels.

In an embodiment of the invention, the battery 39 is comprised of two rechargeable coin cells connected placed in parallel. For example, the battery chemistry can have Lithium-Ion secondary chemistry with a nominal full charged voltage of 3.4 to 3.7 Volts. Battery terminals 22 and 23 may be integrated to the capsule's outer shell and can be fabricated using non-corrosive metals such as gold. Charging terminals can be located on the side of the capsule assembly. In an embodiment, to activate the capsule, the battery is charged prior to use by piercing the capsule's compliant outer shell with pointed charging terminals aligned with the battery terminal locations of the capsule. In this embodiment, the capsule battery terminals are covered by a self-healing silicone rubber compound that maintains the capsules outside seal when the charging terminals are removed once charging is completed.

The second housing 2 laboratory can also be powered by a disposable battery 39 which is comprised of one or more non-rechargeable coin cells or rechargeable battery chemistry cells may be used as illustrated in FIG. 3.

Figure 4:
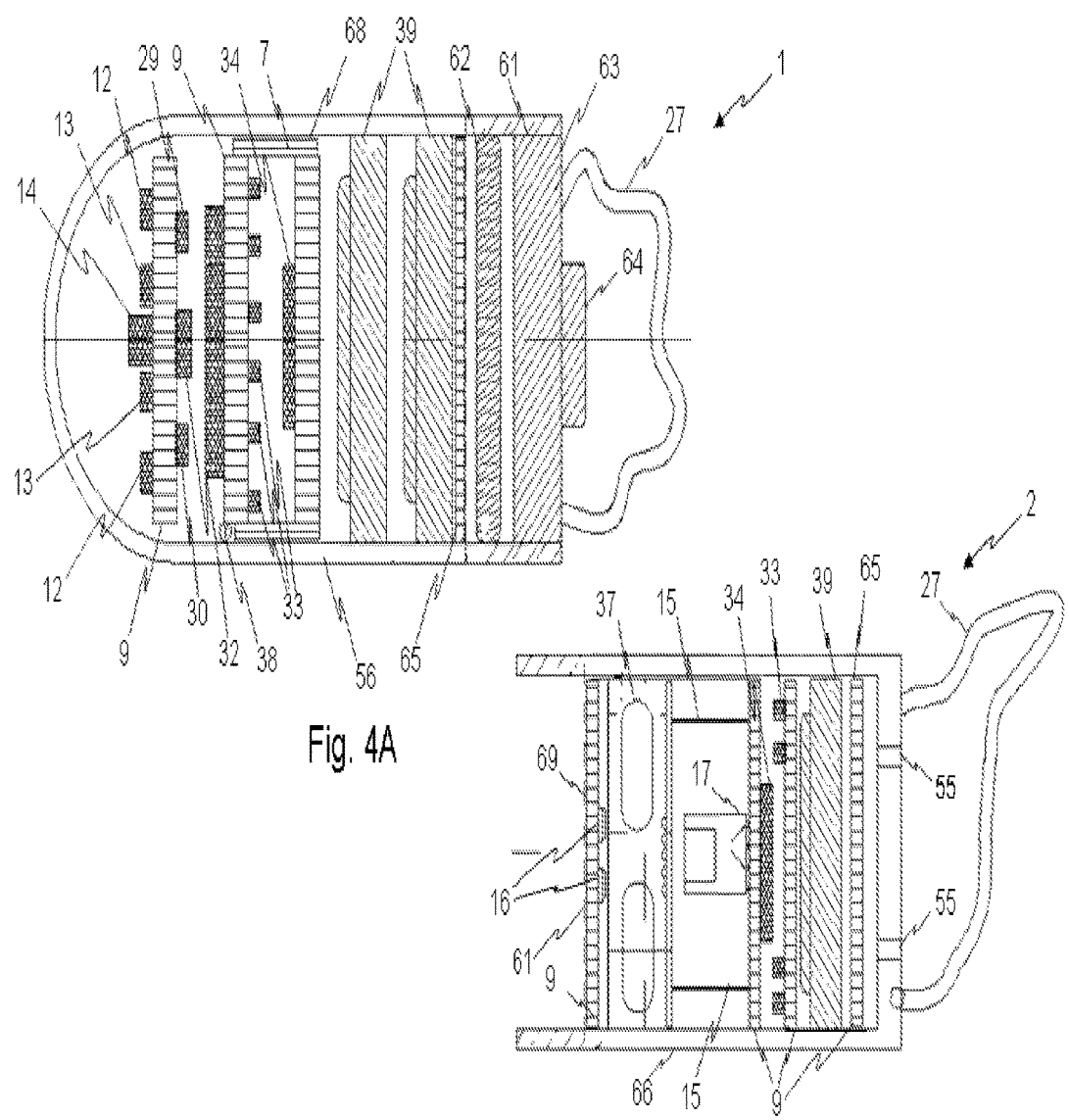
FIG. 4A is a cross-sectional view of a first housing according to an embodiment of the present invention, take along a longitudinal axis.
FIG. 4B is a cross-sectional view of a second housing according to an embodiment of the present invention, take along a longitudinal axis.
Figure 5:
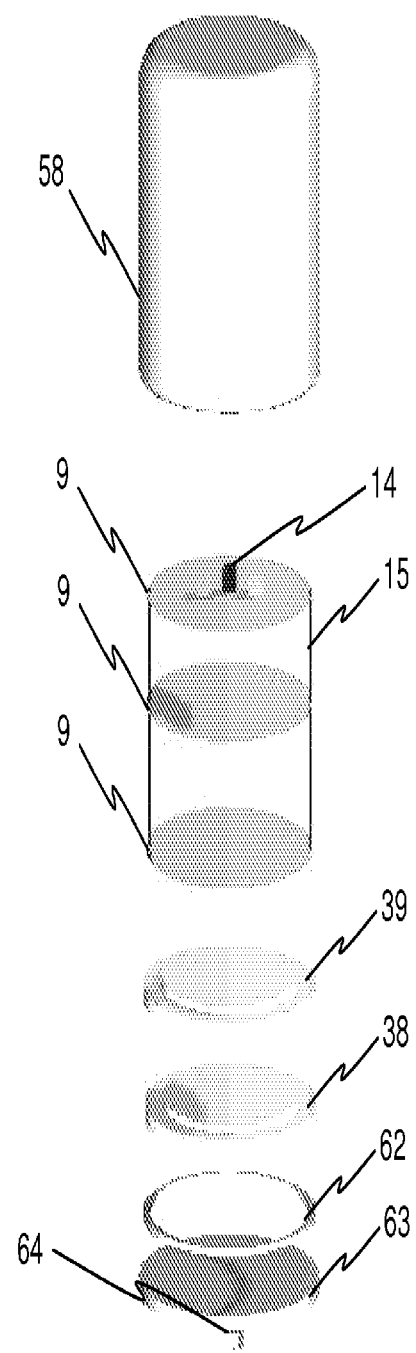
FIG. 5 is an exploded-view illustration of components of a device according to an embodiment of the present invention.
Figure 12:
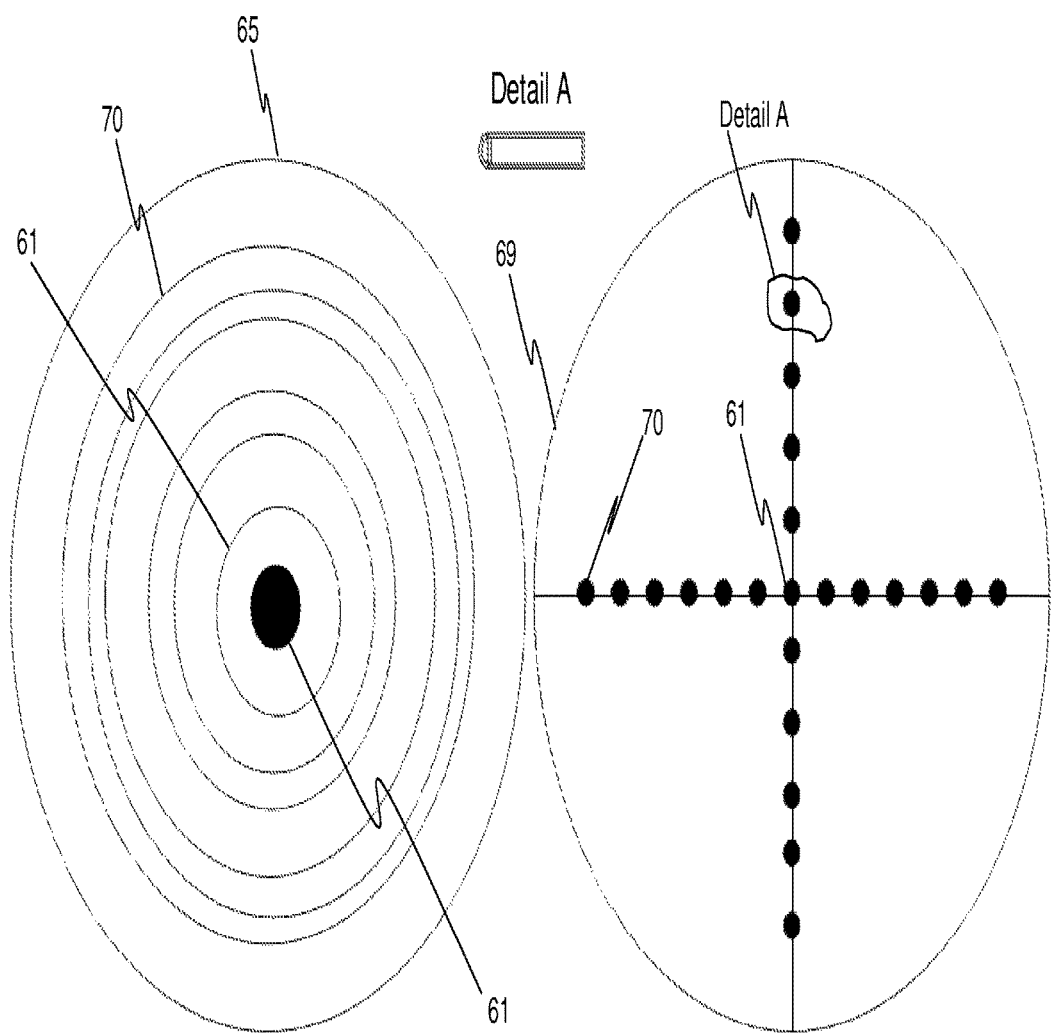
FIG. 12 is a functional-end view of a power and data interface for a device according to an embodiment of the present invention and a detail side view of a pin.
Figure 13:
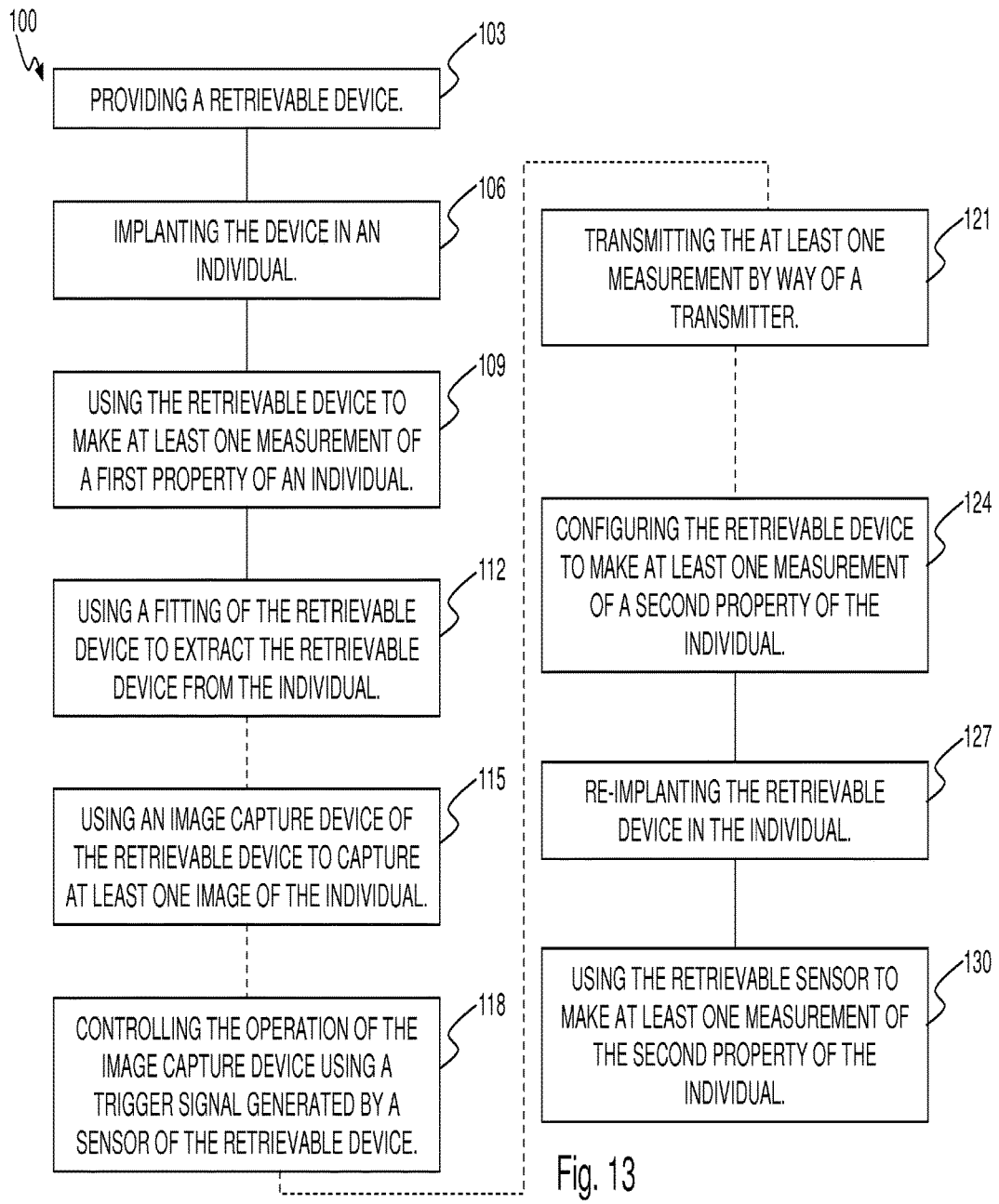
FIG. 13 is a flowchart describing a method according to an embodiment of the present invention.

FIGS. 4, 5 and 12 illustrate additional detail unique to the modular approach for this invention. FIG. 4 illustrates an embodiment of both the stand alone sensing module in the first housing 1 and the chemical sensing module in the second housing 2. Standalone operation end cap 63 with molded grip 64 is fitted to the capsule as shown. This cap may be screwed on to the capsule or a molded snap arrangement may be used to secure the cap. The cap can easily be removed (for battery replacement or charging) using molded grip feature 64. Sealing of the capsule may be accomplished using a thin "O" ring 62. A power switch 61 is incorporated into both the cap and the power and interface board 65. For standalone operation of the first housing 1 the power switch can be formed using the center and first etched conductive concentric rings of the interface board 65. Pins on the cap Detail A can short these two connection points activating the module. In an embodiment, this approach provides 4 connection points for each ring eliminating alignment issues.

The interface board set 65 & 69 in FIG. 12 may contain as many concentric rings and pins necessary to provide a data interface between the chemical sensing unit module 66 of the second housing 2 and first housing 1. The second housing 2 may contain its own microprocessor to process and format the sensed data. This information is then transferred to the first housing 1 for wireless transmission to a receiving device. Both of these modules as well as the composite capsule can be fabricated using a rigid flex PCB configuration. See FIGS. 8 and 9. The location and number of components will differ for each embodiment.

FIG. 5 illustrates one assembly sequence for the first housing 1. This assembly method can simplify the assembly, thereby reducing cost and assembly errors. It also supports subassembly in-process testing to increase reliability and reduce production fallout for the device.

Figure 6:
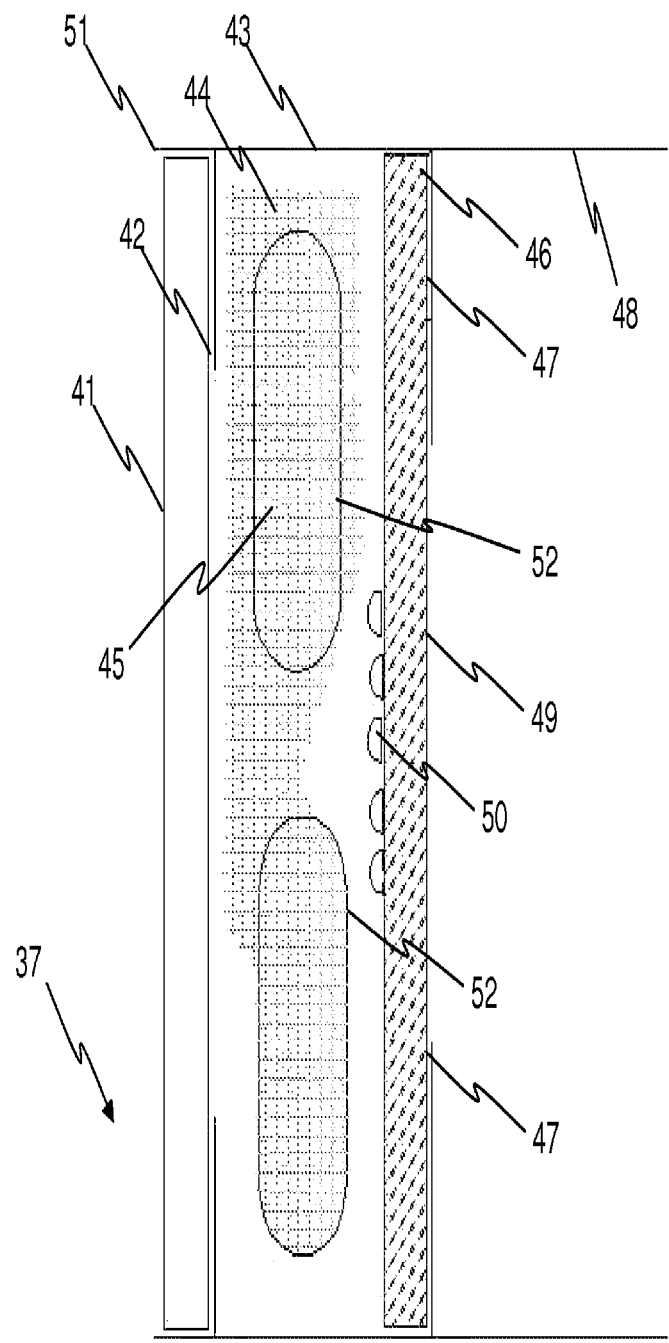
FIG. 6 is a cross-sectional view of a sensor according to an embodiment of the present invention.

FIG. 6 is a detailed drawing of the chemical sensing cell 37 which can be used in either the first housing 1, the second housing 2, or the combination of the housings. The sensing cell 37 can be pre-fabricated and calibrated at the factory. In the example of a modular sensing system, such as in FIG. 3, the sensing cell module can be screwed or snapped onto first housing 1 by the patient and that action may also activates the power switch for both housings to perform laboratory analyses and data reporting. The sensing cell 37 can be comprised of an injection molded circular outer shell 43 with two internal lips 42 and 47. In an embodiment, the front lip 42 has a larger opening diameter while the rear lip 47 has a smaller opening diameter. For example the front lip opening may be 12 mm while the rear lip opening may be 9.6 mm. These features are designed to provide attachment and sealing points for optically clear windows 41 and 49.

The larger front lip opening 42 provides a simple method for assembly of the cell windows from the front of the device through the opening created by lip 42 using a smaller diameter window 49 for the rear of the cell. For example, the diameter of the front window 41 can be 15 mm while the diameter of the rear window 49 can be 11 mm. In another example, both windows are 1.5 mm thick clear optical cast plastic windows offering broad band light transmission of >90%. The front and rear windows 41 and 49 form a liquid tight seal between the sensing cell and the substrates 9 in FIG. 4 of the rigid flex assembly. The length of the outer shell 56 may be such that a lip extends beyond windows 41 and 49 to form an alignment feature for the rigid flex assembly substrates containing the sensor LEDs 16 and the sensor array 17. This feature is illustrated as callouts 51 and 48. The rear window of the cell can face the sensor array 17 and may have an optical filter 46 deposited or attached to it. The sensor substance 50 can also be printed to the inside surface of this window. The sensing cell outer shell 43 may also has elongated slots 52 molded into the circumference of the shell providing a fluid path. The cell can be filled with 0.9% w/v of NaCl, normal saline and a quantity of high molecular weight dextran or suitable alternative to maintain osmotic pressure. The elongated slots 52 can be covered with a semi-permeable membrane 45 that allows fluid flow/exchange to and from the cell.

The first housing 1 or second housing 2 may incorporate a Piezoelectric Polymer Pressure sensing system to measure the amplitude, duration and frequency of contractions occurring in the later months of pregnancy. Details of this sensing system are illustrated in FIG. 7. These sensors can also provide acoustic sensing of patient respiration and heart rate measures from both mother and fetus. Alternatively a small microphone 68 may also be incorporated to provide this function.

In an embodiment, two semi-flexible sensors 7 are located approximately 2 mm from the outer surface 8 of the device and cover approximately 60% of the pills circumference as indicated in the side view in FIG. 7. The outer case of the device can be distortion compliant—meaning it will deform with each contraction. This can be accomplished, for example, by forming the shell using a flexible FDA approved low durometer encapsulant or a semi-rigid plastic shell. The sensors 7 can be comprised of two piezoelectric film foils composed of a polarized fluoropolymer, Polyvinylidene Fluoride (PVDF). The PVDF foils may be separated by a polyimide film insulator 5. Electrical connections to each of the PVDF foils can be accomplished by applying copper foil 4 to the outside surface of each foil. A two wire flexible circuit tail 3 may be soldered to the center of each copper foil 4. Each of these connections is secured and covered using a strip of polyimide film insulator 99. The sandwich assembly can be held together using a flexible elastic adhesive 6 placed on the outer edges of the assembly. The force of a contraction distorts the outer surface 8 which then applies strain to each of the pressure sensors. A small voltage is produced in response to this strain due to the piezoelectric effect. This signal can be processed and filtered by a low noise, JFET operational amplifier 29. The processed signal can be digitized and further processed by microprocessor 34. Temperature compensation for these sensors may be provided using a thermistor 38 which can be located, for example, 2 mm (or a similar distance as the sensors 7) from the outer surface 8. The thermistor 38 can also provide temperature compensation for the LED driver 31, the sensing cell 37, and the accelerometer 32, as well as provide temperature measurement of the proximal environment.

Figure 8:
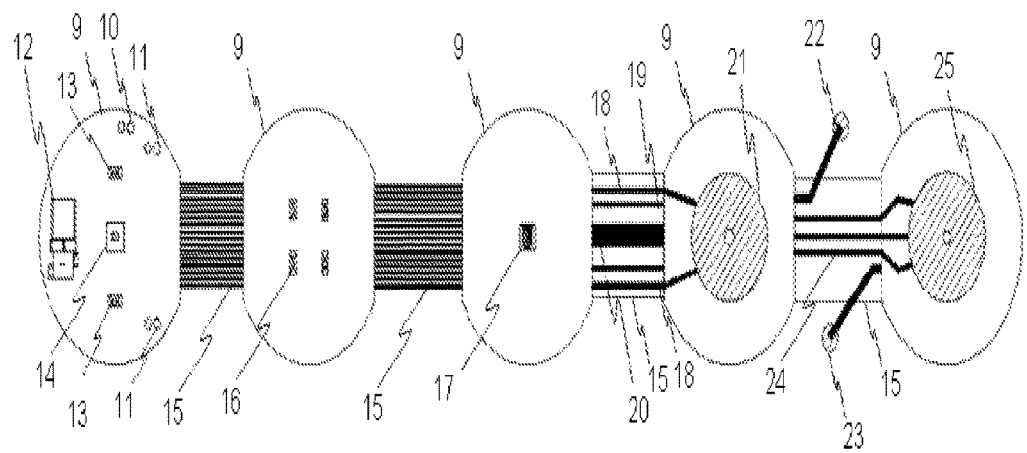
FIG. 8 is a top view of a system board assembly of a device according to an embodiment of the present invention.
Figure 9:
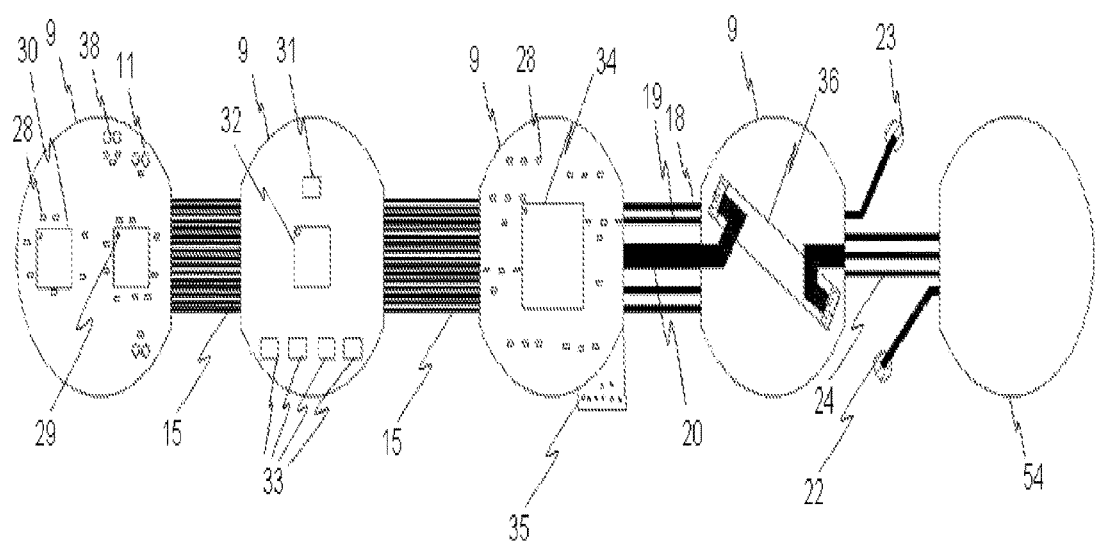
FIG. 9 is a bottom view of the system board assembly of FIG. 8.

FIGS. 8 and 9 illustrate another assembly method for the electronic components supporting multiple embodiments of the present invention. The assembly comprises a series of rigid substrates 9 to which the components in chip scale form are attached to both the top and bottom sides of the substrate. This method produces a rigid flex assembly optimized for manufacturing. The substrates, for example, may be comprised of three layers of FR4 Printed circuit material having a combined thickness of approximately 0.35 mm. The substrates 9 have the necessary conductive paths supporting the circuitry connections and attachment footprints for the integrated circuits and discrete components. The substrates can be interconnected using flexible, insulated fine pitch flat cable assemblies 15 which are embedded into the substrates forming connections through the substrates middle layer to the top and bottom layers and components. This arrangement provides an assembly that can be populated with components using automated assembly techniques when it is in flat form as illustrated in FIGS. 4 and 5 but can be folded into a form for molding into a capsule shape or for insertion into a pre-molded outer shell.

The top side of the rigid flex assembly is drawn in FIG. 8. The image capture device 14, light source 13 and the light circuitry 12 are located on the topside of the first (left hand side) substrate 9. The topside of the second substrate may provide mounting pads for the sensor cell LEDs 16. The sensor array 17 resides on the top side of the third substrate. The sensor cell 37 can be mounted in the area between these two substrates with terminal 21 forming the negative battery connection and terminal 25 forming the positive battery connection. Terminal 25 may be connected using a flex lead 24 located between the batteries and the substrate 9. External battery terminals 22 and 23 may be formed by plating gold over nickel to the copper flex terminal pads. The location of each of the required discrete components to support each major system function will be determined by optimization of the printed wiring for each substrate. Each substrate 9 may contain components in surface mount technology package form. Multiple ground traces 19 and positive battery traces 18 can be used to reduce noise and power system impedance to support high current pulse loading. The connection between the transceiver input/output can be accomplished using a shielded strip line 20 between the top of the third substrate and the bottom of the fourth substrate where the chip antenna 36 can be mounted.

FIG. 9 illustrates a exemplary component layout for the bottom side of the assembly. The first substrate 9 (left side) may contain the JFET operational amplifiers 29 for processing the piezoelectric pressure sensors output and the thermistor 38 output. The sensor voltage reference and power switch circuitry 53 may also be located on this substrate. Discrete components 28 supporting this circuitry may also located on this substrate surface. Flex tail connections 10, 11 for the piezoelectric sensors 7 and the thermistor 38 may be provided on this substrate. The second, bottom side substrate may provide mounting pads for a three axis accelerometer 32, a sensor LEDs drive circuit 31 and a power switch 33. The third substrate 9 may contain a microprocessor 34 and transceiver integrated circuit in a chip scale package with RF matching components. The flex tail connection between substrates three and four contains the strip line antenna trace 20, power, and ground connections. The antenna 36 may attached to substrate four and the external, positive battery charge connection 23 may also originate from this substrate.

A breakaway tab 35 can also attached to this substrate. This tab contains connections to the microprocessor's 34 interface. This interface can be used for initial device and radio programming and in-process testing during production. After testing is complete the tab can be removed from the substrate 9. The fifth substrate may provide room for additional components which can include flash based memory for data storage of sensed data and video. Use of this on-board memory could increase the battery life by reducing the frequency of data transmissions and will provide a backup record of all data collected during operation.

Folding of the rigid flex assembly can be accomplished, for example, using a mold with features for proper alignment of the substrates if the assembly is to be encapsulated using a 2 part room temperature medium viscosity material. Alternatively, a fixture can be used that will also have alignment features and allow adhesive fixing of the substrates, sensing cell and battery in the final configuration for insertion into a plastic shell.

Figure 10:
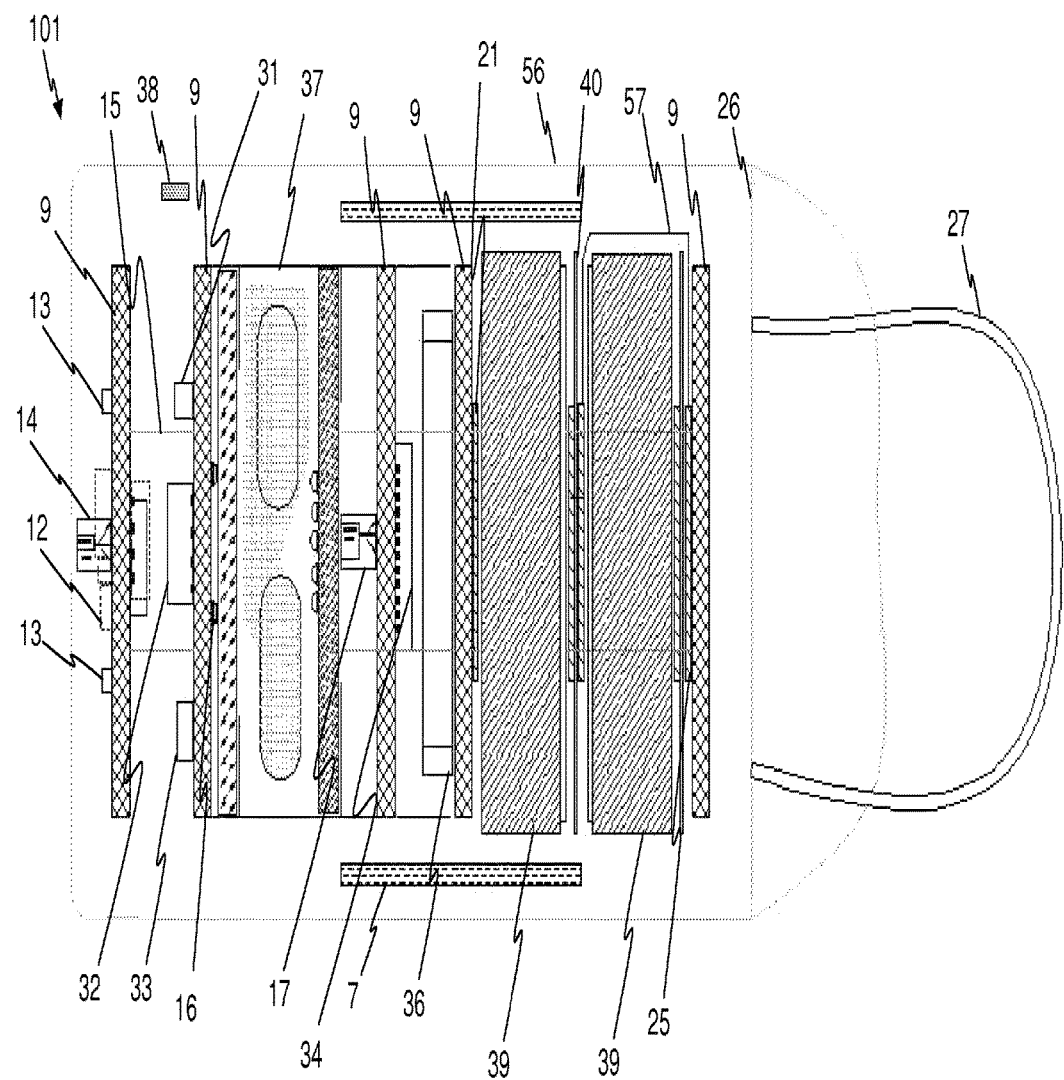
FIG. 10 is a cross-sectional view of a device according to an embodiment of the present invention, take along a longitudinal axis.

The locations of the batteries 39 and sensing cell 37 are clearly illustrated in FIG. 10. The image capture device 14 may require a short focal length lens. Once folded, the flex interconnect cables 15 between the substrates 9 may fall alternately on the front side and back side of the assembly. The parallel connection between the batteries 39 negative terminals can be accomplished using a polyimide film 40 with copper battery terminals. The connection between the positive battery terminal and the top of the fifth substrate can be made using a flex tail 57. The negative battery connection can be carried through the system using the flex tails 15 between the substrates.

Figure 11:
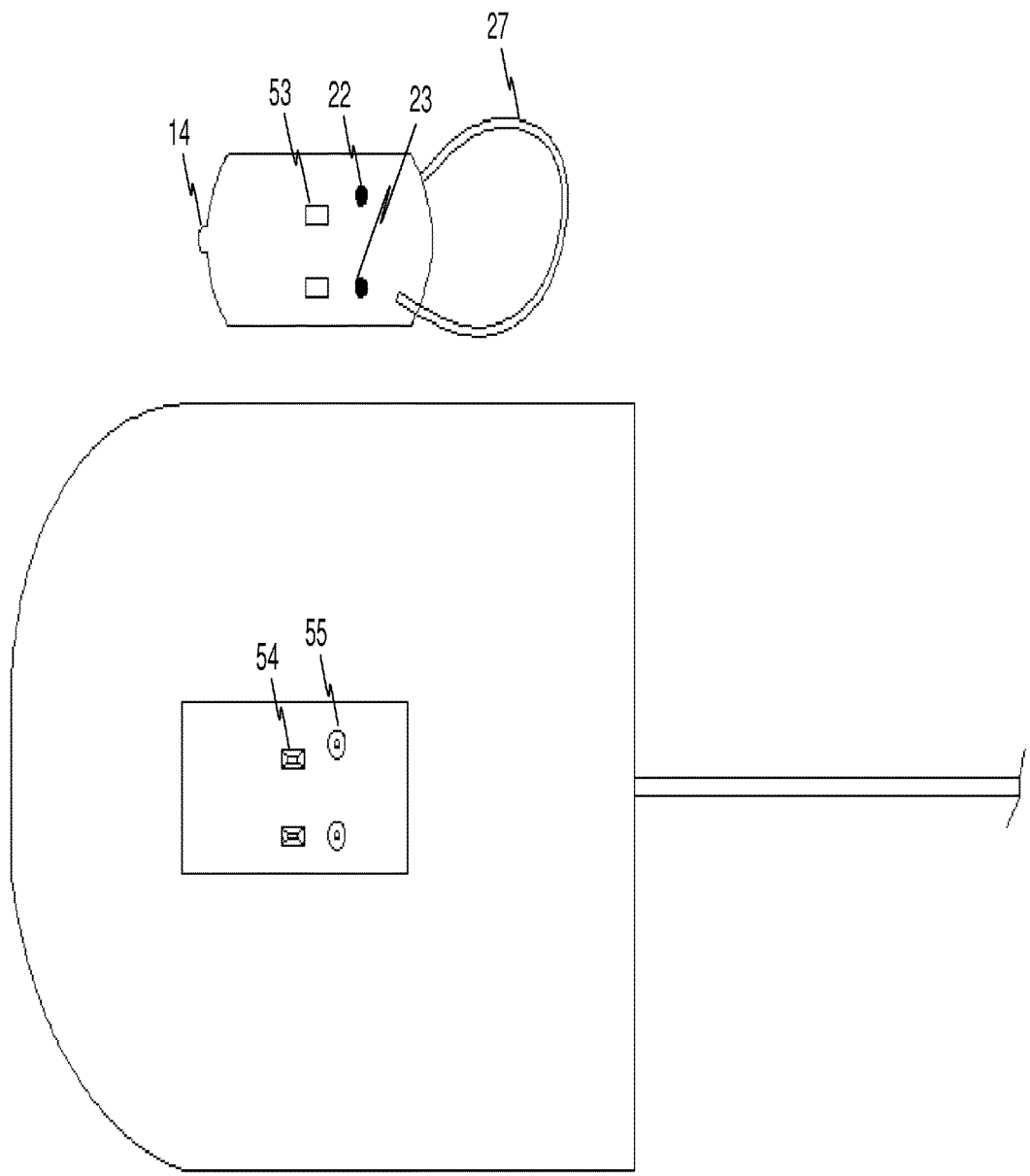
FIG. 11 is an illustration of an embodiment of a charge/calibration stand and a device according an embodiment of the present invention.

Alignment features 53 in FIG. 11 may be added to the encapsulation mold to provide a method for proper alignment of the capsule within the charge/activation stand. These features may, for example, consist of shallow wells molded into the assembly designed to mate with a similar geometric post within the charge/activation stand capsule holding assembly. These will insure that external, battery terminals 22 and 23 will mate properly with the correct polarity of the pointed terminals within the charge/activation stand. If the capsule is not inserted properly into the charge/activation stand then the capsule will sit too high in the stand to allow the pointed terminals to penetrate the capsules shell.

An outer shell outline 56 is indicated in FIG. 10. In this embodiment, thermistor 38 and piezoelectric sensors 7 are located close to the outer shell 56.

In order to facilitate easy removal of the pill, a Dacron™ loop 27 may be provided. The loop can be fixed to the end cap 63 of the first housing 1 and the plastic molded end the second housing 2. When the two modules are screwed or snapped together the loop is internally secured to the end cap of second housing 2 or the capsule body using a small plastic plate 26.

FIG. 11 illustrates an embodiment of the charge/activation and calibration stand for the capsule. The charge/activation stand may comprise a plastic shell containing a capsule fixing well 54 designed to hold capsule for activation calibration and charging. Two post-like features 55 can be included and designed to insure proper alignment of capsule in the stand by mating with alignment wells 54. Two pointed battery charging pins 55 may be provided and designed to pierce the self-healing silicon rubber caps on the capsules battery terminals 22 and 23. The charge/activation and calibration stand may include a radio transceiver designed to monitor and control the capsule during operation. The stand may include a USB to PC interface and a USB powered battery charging circuit. The USB interface can support data display on the PC during operation, data downloading after removal of the pill, and programming of the pill prior to use. A hinged lid designed to hold the capsule in position during charging and calibration can be used to secure the pill during these operations, this feature is not shown in FIG. 11. During operation collected data and pill status can also monitored using a patient worn device such as a wrist watch containing a transceiver and data display or a smart phone with a Bluetooth™ application for data reception, communication with the pill, and display of collected data. The images and video captured by the image capture device 14 are displayed on a monitoring device (e.g., cell phone, PC screen, etc.). The user may optimize picture quality and participate in monitoring their condition and communicating the information to health care providers.

An embodiment of the present invention would not include the chemical sensing system and its associated detector. This embodiment would yield a device capable of measuring patient activity, heartbeats from mother and fetus, vaginal contractions and visual observations of dilation of the cervix. For this embodiment the sample-on-demand functions that may be initiated by the start of a contraction as sensed by the accelerometer, heart rate, temperature and pressure sensors.

Another embodiment for this device would not include the chemical sensing system and its associated detector. This embodiment would include a camera, an accelerometer, and an acoustic and piezo pressure detector. This embodiment would yield a device capable of measuring patient activity, heart rate of mother and fetus, frequency and duration of contractions, and provide photographic images of dilation of the cervix. For this embodiment the sample-on-demand functions that may be initiated by the start of a contraction as sensed by the accelerometer and temperature sensors.

Embodiments of the present invention also include, without limitation, the following examples and combinations thereof:

EXAMPLE 1

An implantable vaginal capsule for use in measurements of signals within the vaginal tract of a mammal, comprising, an electric power source, a radio signal transmitter/receiver, and enabling circuitry with said power source suitable for transmitting a radio signal, and a source of said signal. The integrated radio communications assembly provides the device with the ability of accepting external commands via radio transmission, said external control of all data storage, transmitting, collection methods and data sampling rates, said external control to provide device status or change transmission modes on request. An internal operating program that provides the ability to pre-program capsule responsiveness to events including sensor sampling rate adjustment and CMOS sensor and digital camera operation based on sensed data thresholds. All of the functional components of the implantable vaginal capsule are encased in a non-digestible outer shell that is configured to remain present in said vaginal canal while taking its measurements of said signals.

EXAMPLE 2

The implantable vaginal capsule of Example 1, wherein the device is powered using coin cell type primary chemistry batteries and device activation is accomplished using an etched switch arrangement contained within the end cap of the device.

EXAMPLE 3

The implantable vaginal capsule of Example 1, wherein the signal is digitized still frame or video sequence of images of the anatomical components of the vaginal canal or associated components of the internal environment including but not limited to fluids, blood and blood components, lesions, abnormal anatomical structures such as carcinomas, and introduced radio-opaque substances employed for radiographic imaging, and not limited to additional imaging within the capability of present and future digital imaging technology.

EXAMPLE 4

The implantable vaginal capsule of Example 1, wherein the signal is a physical measurement such as temperature, acoustic signals, pressure, and movement in three dimensional space.

EXAMPLE 5

The implantable vaginal capsule of Example 1, wherein the signal is a chemical measurement from a measurement sensor specific to that chemical, and having output signals that may be stored, processed, and/or transmitted by the radio components of said vaginal capsule.

EXAMPLE 6

The capsule of Example 1, wherein said electric power source comprises one or more of a secondary chemistry coin shape battery having battery terminals sealed using self healing silicone rubber covers.

EXAMPLE 7

The capsule of Example 1, wherein said transmitter emits a radio frequency (RF) signal, detectable outside of the shell of the capsule, when enabled by said power source.

EXAMPLE 8

The capsule of Example 1, wherein said power source consumption is controlled by "smart software," the software employing numerous power modes to extend battery life.

EXAMPLE 9

The capsule of Example 1, wherein software monitors the received data error rate for each data transmission and such information is used by an adaptive RF power algorithm to adjust transmitter radio frequency (RF) transmission power output thus saving battery power by reducing the number of retransmissions required.

EXAMPLE 10

The capsule of Example 1, wherein internal non-volatile memory is used for the storage of sensed data and photographic images.

EXAMPLE 11

The capsule of Example 1, wherein said receiver provides direct control of radio frequency (RF) transmission modes including burst type transmission to reduce power consumption.

EXAMPLE 12

The capsule of Example 1, wherein said receiver allows external commands to request transmission of capsule battery status, sensor and memory status, control of onboard CMOS camera mode and operation, sensor sampling rate, and control of optical drive for the sensors.

EXAMPLE 13

The capsule of Example 1, wherein said receiver/transmitter is capable of operation over 256 RF digital channels providing the capability of monitoring multiple capsules operating in close proximity without interference.

EXAMPLE 14

The capsule of Example 1, that uses a chemical sensing method to detect chemicals in the fluids of the vaginal tract for the entire time it is present in said vaginal tract.

EXAMPLE 15

The capsule of Example 14, wherein said chemical sensing mechanism uses spectroscopic detection of analytes. More particularly, the present invention provides a device wherein the electromagnetic radiation generator provides a substrate for chemical sensors, and wherein the spectroscopic properties of the chemical sensors are modified upon contacting an analyte.

EXAMPLE 16

The capsule of Example 14, which provides a method for the selective and simultaneous detection and continuous quantification of multiple analytes, and a method of making the device useful in the vaginal tract of an animal by incorporating a semi-permeable membrane to separate undesirable substances from the continuously functioning sensor sites.

EXAMPLE 17

The capsule of Example 14, having one or more chemical sensors for interacting selectively with a particular analyte in a sample. In the absence of the analyte, the chemical sensor displays certain baseline spectroscopic properties characteristic of the sensor. However, when the analyte is present in the sample, the spectroscopic properties of the chemical sensor are modified. Detection and quantification of the analyte are based on a comparison of the modified properties and the baseline properties.

EXAMPLE 18

The capsule of Example 14, wherein a chemical sensor comprises a reporter molecule whose spectroscopic properties are modified in the presence of an analyte. The properties of the reporter molecule may be directly modified upon its interaction with the analyte. Alternatively, the reporter molecule may be attached to a template material having a specific affinity for the analyte, in which case, the optical properties of the reporter molecule are modified upon the interaction of the template material with the analyte. Thus, by the term "spectroscopic properties of the chemical sensor" or "chemical sensor's spectroscopic properties" is meant the spectroscopic properties of the reporter molecule and vice versa. These properties may be optical in nature when the emitted electromagnetic radiation is within the visible spectrum, for example between about 400 nm to about 800 nm. For example, the chemical sensor could be a site selectively templated and tagged xerogel (SSTTX), a protein imprinted xerogel with integrated emission site (PIXIES), a surface bound antibody to a chemical, or protein with an attached reporter. The reporter molecule may be one or more photo luminescent reporter molecules within a molecularly templated xerogel and the analyte affinity is afforded by the template sites within the xerogel. In another embodiment, the chemical sensor is a luminescent ruthenium based dye (tris(4,7-diphenyl-1,10-phenanthroline)ruthenium(II), ([Ru(dpp)3]2+), and the reporter molecule ([Ru(dpp)3]2+) provides an analyte-dependent photoluminescence response directly.

EXAMPLE 19

The capsule of Example 14, whereby types of analytes that may be detected include both liquid and gaseous materials. These include $CO_2$, $O_2$, glucose, creatinine, prolactin, cystatin-A, Human chorionic gonadotropin (HCG), cytokines (IFN-gamma, IL-1, IL-6, IL-8, IL-10 and IL-12), other interleukins, peptides, carbohydrates, hormones such as estrogens, progesterones, Luteinizing Hormone (LH) or Lutropin, Follicle-Stimulating Hormone (FSH) and other fertility biomarkers, hemoglobin, proteins, peptides, pesticides, drugs, herbicides, anions, cations, antigens, oligonucleotides, fetal fibronectin, Alpha-fetoprotein (AFP, α-fetoprotein; also sometimes called alpha-1-fetoprotein or alpha-fetoglobulin) and haptens. Proteins used as biomarkers for diagnosis of cancer in the cervix, uterus or ovary may be detected and used with or without images of the cervix for diagnosis, and be within the scope of the invention. Further, the present invention can indicate the pH and salinity of the fluids of the vaginal canal. In another embodiment of the invention, chemical sensors are available and can be used in the present invention to detect the presence of organic molecules such as polycyclic aromatic hydrocarbons, glucose, ketones, amines, amides, cholesterol, amino acids, and peptides. Further, the present invention can detect the presence of bacteria and viruses of both normal and pathogenic nature. There are many more substances which can be detected, and the foregoing list is not to be considered exhaustive, but instead is merely representative.

EXAMPLE 20

The capsule of Example 14, whereby the analyte-dependent spectroscopic signature from the chemical sensor may be detected. One configuration utilizes a detecting device in combination with a receiving and interpreting system. The receiving and interpreting system has a receiver to receive electromagnetic radiation transmitted or emitted by the chemical sensor(s) and convert the optical signal into an electrical signal. An interpreter interprets the received electrical signal. In an embodiment, an optical signal receiver is a complementary metal oxide semiconductor (CMOS) based array with a filter preceding the receiving surface on the CMOS array. The interpreter may include a controller and a computer having software running thereon. In this example, the receiving surface is connected to the controller.

EXAMPLE 21

The capsule of Example 14, wherein one or more electromagnetic radiation filters may be placed between the substrate and the receiving surface. The filter selectively passes desired wavelengths of the electromagnetic radiation moving from the detecting device toward the receiving surface and blocks undesired wavelengths. One example of a filter which can be used for this example is model number Fire #19 manufactured by Roscolux of Stamford, Conn. This particular filter passes electromagnetic radiation above approximately 515 nm and strongly attenuates electromagnetic radiation below approximately 480 nm. Other gel type thin film filters or holographic notch filters can also be used for this purpose. Other filters or filter combinations are possible depending on the generator wavelength and the particulars associated with a given sensor.

EXAMPLE 22

The capsule of Example 14, wherein the sample to be analyzed is continuously exposed to the chemical sensor(s), and the receiver components are placed in the proper position to permit the receiving and interpreting system to receive radiation from said chemical sensors.

EXAMPLE 23

The capsule of Example 14, wherein the electromagnetic information collected during operation is digitized to provide input to a digital memory during sensing, and sent to a receiving device over wireless communications at time intervals.

EXAMPLE 24

The capsule of Example 14, using SSTTX-, or PIXIES-, or antibody capture based surface sensors. The analyte-dependent spectroscopic signal from these types of sensors is stable for many days under constant excitation or intermittent excitation at timed intervals. Thus, the chemical sensor platform is sufficiently stable to be used for detection and quantification of analytes in the fluids of the vaginal tract over an extended time period.

EXAMPLE 25

The capsule of Example 14, wherein the present example provides a detecting device wherein the chemical sensor can be placed in contact with the electromagnetic radiation generator that excites the luminescent reporter molecules within the sensors, making the device compact and suitable for incorporation in the capsule of Example 4. Furthermore, the electromagnetic radiation used in the present invention is not reflected, filtered, or transmitted over a long distance prior to reaching the chemical sensors. In addition, the detecting device according to the present example can be made relatively inexpensively and readily mass produced.

EXAMPLE 26

The capsule of Example 25, wherein said xerogel-based sensor platform continuously detects one or more analyte molecules in vaginal fluids in relation to concentration, and wherein analyte-dependent spectroscopic signal by the sensors occurs in strength proportional to analyte concentration in vaginal tract fluids.

EXAMPLE 27

The capsule of Example 25, wherein the vaginal fluid sample contained may be removed and submitted to an external laboratory for chemical or genetic analysis in order to facilitate a medical diagnosis or a medical treatment decision.

EXAMPLE 28

The capsule of Example 25, wherein said xerogel-based sensor platform associates and dissociates reversibly to its analyte molecule, enabling continuous signal emulation in proportion to changing concentration of said analyte molecules in vaginal fluids.

EXAMPLE 29

The capsule of Example 25, wherein said molecular analysis substance is any other composite or molecule which binds to its configured specific analyte surface, enabling spectroscopic signal emulation in relation to concentration of said analytes or said molecules in vaginal fluids of a mammal.

EXAMPLE 30

A capsule device for repeated detection of the concentration of at least one analyte in a sample, comprising: an electromagnetic radiation generating source having at least one SSTTX-, PIXIES-, or antibody capture-based sensor formed directly on a substrate that is in turn in close proximity to the electromagnetic radiation generating source, such that the analyte-containing fluid can come into contact with the sensor, wherein the spectroscopic properties of the chemical sensor are modified in the presence of said analyte.

EXAMPLE 31

The device of Example 30, wherein the electromagnetic radiation generating source is a light emitting diode.

EXAMPLE 32

The device of Example 30, further comprising a receiving and interpreting system having an electromagnetic radiation receiver to receive electromagnetic radiation emitted by the sensors, and configured to interpret the received electromagnetic radiation.

EXAMPLE 33

The device of Example 30, wherein the receiver includes a filter for selectively passing electromagnetic radiation.

EXAMPLE 34

The device of Example 30, wherein the chemical sensing mechanism is fabricated as a pre-assembled apparatus containing xerogel-based sensing sites, wavelength filter, clear sealing windows, alignment features for radiation source and, detector.

EXAMPLE 35

The capsule of Example 1, wherein the chemical sensing cell of Example 34 is filled with normal (0.9%) saline and covered with a semi-permeable membrane allowing communication between the membrane to be sensed and the chemical sensing sites configured using an equilibration process.

EXAMPLE 36

The capsule of Example 1, incorporating the chemical sensing cell of Example 34 wherein the wavelength filter is deposited to the surface of one of the optically clear seals, and the xerogel-based sensing sites are printed directly onto this surface.

EXAMPLE 37

The device of Example 30, wherein the receiver includes a complementary metal oxide semiconductor (CMOS) based array charge coupled device.

EXAMPLE 38

The device of Example 30, wherein the receiver includes a lens for focusing the electromagnetic radiation on the charge coupled device.

EXAMPLE 39

The device of Example 30, wherein the receiver includes an opaque shield above the lens for focusing the electromagnetic radiation on a complementary metal semiconductor (CMOS) based array device.

EXAMPLE 40

The device of Example 30, wherein the interpreter includes a storage component for storage for digitized data output from the complementary metal oxide semiconductor (CMOS) array.

EXAMPLE 41

The device of Example 30, further comprising a holding substrate for holding the chemical sensors in optical alignment with the electromagnetic radiation generating source, one or more filters, and a receiver.

EXAMPLE 42

The device of Example 41, wherein the holding substrate is a xerogel or other material (e.g., glass, plastic, etc.) that is not degraded in the fluids of the vaginal tract.

EXAMPLE 43

The device of Example 42, wherein the holding material is comprised of tetramethylorthosilane.

EXAMPLE 44

The device of Example 30, wherein the chemical sensor(s) is(are) comprised of a reporter molecule and an analyte-responsive template (e.g., SSTTX or PIXIES, etc.) having a specific affinity for the analyte.

EXAMPLE 45

The device of Example 30, wherein the reporter molecule is selected from the group consisting of fluorophore, phosphore, chromophore, and/or Raman scatterer.

EXAMPLE 46

The capsule of Example 1, wherein the capsule's internal signal measurement device can detect physical changes in temperature, pH, vaginal fluid viscosity, three axis movement, acoustic signals, pressure changes associated with the contraction and relaxation of vaginal walls and structures, and capture visual images of internal structures as recorded with a digital still and video camera.

EXAMPLE 47

The measurement system of Example 46, wherein the pressure measurement is detected using two piezoelectric polymer foil pressure sensors located near the surface of the capsules outer shell and covering approximately 60% of the capsules circumference.

EXAMPLE 48

The pressure measurement system of Example 46, wherein temperature compensation of the sensors and the temperature of the vaginal canal is measured using a temperature sensor located near the surface of the capsules outer shell.

EXAMPLE 49

The capsule of Example 1, wherein acoustic signals are detected using the piezo pressure sensors or a small MEMS based digital microphone. Microphones of this type are currently available in form factors that occupy less that 0.7 mm of space making them ideal for this application. Said acoustic signals include but are not limited to heart rate, breathing cycles and bowel sounds.

EXAMPLE 50

The capsule of Example 46, wherein the measurement and record of patient movement and physical activity is determined using a three axis accelerometer.

EXAMPLE 51

The capsule of Example 1, wherein the capsule contains a remote actuatable storage reservoir which comprises a radio signal receiver configured to receive a signal from a remote transmitter positioned exterior of said outer shell of said capsule.

EXAMPLE 52

The transmitter of Example 51, contained in a form factor that can be worn by the patient as a wrist watch or incorporated as a Bluetooth™ application for a smart phone.

EXAMPLE 53

The capsule of Example 1, wherein said outer shell comprises a low durometer plastic encapsulant or thin polycarbonate shell.

EXAMPLE 54

The capsule of Example 1, that will provide chemical sensing on a continuous basis in any fluid containing environment of animals.

EXAMPLE 55

The capsule of Example 1 that will provide sensing in any environment where external temperature is −10 to 75 degrees centigrade.

EXAMPLE 56

The capsule of Example 1, wherein said enabling circuitry comprises a rechargeable battery and self sealing connections to an external battery charging system to act as a switch.

EXAMPLE 57

A vaginal capsule for insertion into the vaginal canal comprising, a non-digestible outer shell; an electric power source; a radio signal transmitter/receiver with enabling circuitry; said power source suitable for transmitting a signal; the capsule capable of detecting changes in vaginal pH, pressure, temperature, motion, acoustic signals, and visual conditions of structures such as the cervical opening to the uterus of a mammal.

EXAMPLE 58

The device of Example 57, wherein a quantified DC voltage signal is digitized to provide input to a computer.

EXAMPLE 59

The device of Example 57, wherein a time multiplexed output of the multiple sensors is converted to an intermediate frequency signal, quantified as a DC voltage signal and digitized to provide input to a computer.

EXAMPLE 60

The device of Example 57, wherein said transmitted signals are received exterior of the animal body digitized and provided to a computer.

EXAMPLE 61

The device of Example 57, wherein said digitized information has data regarding the length of time of said capsule in said canal.

EXAMPLE 62

The process of Example 56, wherein said computer is programmed to scan and compute variations from pre-programmed factors.

EXAMPLE 63

The process of Example 57, wherein said capsule receiver/transmitter can accept external commands during operation to change sensed parameter sampling rates, activate the digital camera, or report status of the capsule's systems.

EXAMPLE 64

A process for the continuous collection of sensing data in the vaginal canal of an animal comprising: providing an insertable capsule containing a microprocessor suitable for determining measurements and storing data; receiving a transmitted signal exterior of the body of said animal; digitizing said signal received by said microprocessor; storing said digitized signal in computer recoverable, time sequence memory.

EXAMPLE 65

An insertable capsule for continuous collection of sensing data in the vaginal canal of an animal comprising, a non-digestible outer shell; an electric power source; a radio signal transmitter in enabling circuitry with said power source suitable for transmitting a radio signal the location from which it emanates in said canal.

EXAMPLE 66

The capsule of Example 64, comprising a measurement device to measure sensing signals from vaginal fluids, and said output is converted to time multiplexed output.

EXAMPLE 67

The vaginal capsule of Example 1, with an electronic data capture and processing configuration incorporating sensors, used for monitoring of a pregnancy in a female mammal.

EXAMPLE 68

The vaginal capsule of Example 1, with an electronic data capture and processing configuration incorporating sensors for glucose, used for monitoring of diabetes in a female mammal.

EXAMPLE 69

The vaginal capsule of Example 1, with an electronic data capture and processing configuration incorporating sensors, used for monitoring of fertility, for use in natural contraception, or natural contraception.

EXAMPLE 70

The vaginal capsule of Example 1, with an electronic data capture and processing configuration incorporating sensors, used for a monitoring of and adjustment of hormonal balance in pre-menopausal female mammals.

EXAMPLE 71

The vaginal capsule of Example 1, with an electronic data capture and processing configuration incorporating sensors, used for monitoring of and adjustment of hormonal balance in post-menopausal female mammals.

EXAMPLE 72

The vaginal capsule of Example 1, with an electronic data capture and processing configuration incorporating sensors, used for monitoring of vaginal bleeding and associated conditions in female mammals.

EXAMPLE 73

The vaginal capsule of Example 1, with an electronic data capture and processing configuration incorporating sensors, used for monitoring of organic sexual dysfunction of the female genital tract of a mammal.

EXAMPLE 74

The vaginal capsule of Example 1, with an electronic data capture and processing configuration incorporating sensors, used for monitoring of vaginal and uterine cramping in female mammals.

EXAMPLE 75

The vaginal capsule of Example 1, with an electronic data capture and processing configuration incorporating sensors, used for monitoring of subject heart rate and breathing cycles.

EXAMPLE 76

The vaginal capsule of Example 1, with an electronic data capture and processing configuration incorporating sensors, used for monitoring of vaginal inflammation or infections of the female genital tract of a mammal.

EXAMPLE 77

The vaginal capsule of Example 1, with functional components excluding the chemical measurement sensors, used for measurement of physical processes inside the female genital tract of a mammal and incorporating video or digital image capture.

EXAMPLE 78

The capsule of Example 1, with functional components including or excluding the chemical measurement sensors, used for measurement of physical processes inside the rectal orifice of a mammal and incorporating video or digital image capture.

EXAMPLE 79

The capsule of Example 1, with functional components including or excluding the chemical measurement sensors, used for measurement of physical processes inside the oral orifice of a mammal and incorporating video or digital image capture.

EXAMPLE 80

The capsule of Example 1, wherein the electronic components used within the capsule are contained on a series of rigid substrates interconnected with fine pitch flat flexible wiring.

EXAMPLE 81

The capsule of Example 80, wherein the rigid flex assembly is designed to be folded providing proper alignment of all components and insertion into an outer protective shell.

EXAMPLE 82

The capsule of Example 80, wherein the folded assembly is inserted into a mold and the outer shell is encapsulated using an FDA approved 2-part medium viscosity compound.

EXAMPLE 83

The capsule of Example 80, wherein a multi-purpose capsule activation stand that communicates with a PC via a USB port is used prior to capsule use to charge the capsules internal battery, calibrate the capsules sensors, and test all inter-capsule functions, and function as a receiver for the capsule during normal operation.

EXAMPLE 84

The multi-purpose capsule activation stand of Example 83, wherein the multi-purpose capsule activation stand is used to program the capsule. Programmed functions will include setting sensed data thresholds for event triggering: such as activating on board cameras, setting the transmit and receive RF channels for the capsules transceiver, setting sensor sample rates and sample rate changes due to sensed data thresholds being met.

EXAMPLE 85

The capsule of Example 1, wherein external communication with the capsule for both receiving capsule data and controlling the capsules cameras, sensor sampling rate and power mode are provided using a transceiver having a USB thumb drive form factor connected to a PC.

EXAMPLE 86

The capsule of Example 1, wherein external communication with the capsule for both receiving capsule data and controlling the capsules cameras, sensor sampling rate and power mode are provided using a patient worn small battery powered transceiver and data collection device providing maximum patient mobility. Data collected may be downloaded to a PC upon completion of the test.

EXAMPLE 87

The capsule of Example 1, wherein external communication with the capsule for both receiving capsule data and controlling the capsules cameras, sensor sampling rate and power mode are provided by a application running on a "Smart Phone" or other hand held personal communication device.

EXAMPLE 88

The capsule of Example 1, wherein the said enabling circuitry comprises a polymeric seal about conductive terminals to charge and/or activate the battery prior to use and provide removal, cleaning, recharge and reinsertion patient cycles without compromising device integrity.

EXAMPLE 89

The capsule of Example 1, wherein the components of module 2 illustrated in FIG. 3 can be replaced with a new module by a simple procedure, creating a disposable laboratory component to the vaginal capsule assembly. A further embodiment of the capsule in Example 1 does not include the chemical sensing system and detector.

EXAMPLE 90

The capsule in Example 89, that provides a sample-on-demand function based upon a pre-defined sensing threshold for the imaging, pressure, accelerometer, acoustic, and temperature sensors.

EXAMPLE 91

A further embodiment of the capsule in Example 1 that does not include the chemical sensing system or the piezo pressure sensor.

EXAMPLE 92

The capsule in Example 91 that provides a sample on demand function based upon a pre-defined sensing threshold for the accelerometer and temperature sensors.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A retrievable device for in vivo monitoring of a pregnant individual, comprising:
    a first housing having a light source configured to illuminate at least a portion of a cervical opening of the individual, an image capture device positioned to capture an image of at least a portion of the cervical opening of the individual, a 3-axis accelerometer, a connector configured to removably connect to a second housing, and a data interface configured to communicate with a mating data interface of the second housing;
    a tether attached to the first housing for retrieving the device;
    wherein the first housing is configured to be inserted in a vaginal tract, retrieved from the vaginal tract, and reconfigured with one or more additional sensors before reinsertion in the vaginal tract;
    the device further comprising a second housing having a sensor, the second housing having:
    a mating connector configured to cooperate with the connector of the first housing for removable connection with the first housing; and
    a mating data interface configured to cooperate with the data interface of the first housing for communication with the first housing; and
    wherein the sensor is an analyte sensor configured to obtain at least one measurement of a concentration of analyte in a vaginal fluid of the individual, the analyte sensor:
    a) comprising a sensor substance in a sol-gel material such that the sensor substance reversibly interacts with an analyte of interest, the sensor substance configured to emit electromagnetic energy when the analyte of interest is in contact with the sensor substance and electromagnetic excitation energy is received by the sensor substance; and
    b) configured to be in contact with the vaginal fluid.

2. The device of claim 1, wherein the accelerometer is electrically connected to the image capture device, the accelerometer being configured to generate a signal for controlling the operation of the image capture device.

3. The device of claim 1, wherein the sensor is an analyte sensor configured to obtain at least one measurement of a concentration of analyte in a vaginal fluid of the individual, the analyte sensor:
    a) comprising a sensor substance in the form of an antibody bonded to a reporter molecule such that the antibody interacts with an analyte of interest, the reporter configured to emit electromagnetic energy when the analyte of interest interacts with the antibody; and b) configured to be in contact with the vaginal fluid.

4. The device of claim 1, wherein the analyte sensor is configured to continuously measure a concentration of analyte in the vaginal fluid.

5. The device of claim 1, wherein the analyte sensor further comprises:
a detector configured to detect electromagnetic energy emitted by the sensor substance; and
a controller in electronic communication with the detector for measuring a concentration of analyte based on the detected electromagnetic energy.

6. The device of claim 1, wherein the analyte sensor further comprises an electromagnetic excitation energy source configured to provide electromagnetic excitation energy to the sensor substance.

7. The device of claim 1, further comprising one or more sensor modules configured to be removably connected between the first housing and the second housing, each of the one or more sensor modules having at least one additional sensor.

8. The device of claim 7, wherein at least one of the one or more sensor modules are configured to detect multiple analytes.

9. The device of claim 1, wherein the first housing further comprises a parametric sensor for measuring a physical parameter of the environment external to the second housing.

10. The device of claim 9, wherein the parametric sensor comprises a piezoelectric pressure sensor.

11. The device of claim 9, wherein the physical parameter is sound, pH, temperature, or pressure.

12. The device of claim 1, further comprising a transmitter and/or a receiver for communicating with an external device.

13. The device of claim 1, further comprising a receiver in electronic communication with the image capture device and the image capture device captures an image based on a signal from the receiver.

14. The device of claim 1, further comprising an electronic storage device electrically connected to the image capture device.

15. A method of in vivo monitoring of a pregnant individual, comprising the steps of:
providing a retrievable device comprising:
a first housing having a light source configured to illuminate at least a portion of a cervical opening of the individual, and an image capture device positioned to capture an image of at least a portion of the cervical opening of the individual, a 3-axis accelerometer electrically connected to the image capture device, a connector configured to removably connect to a second housing, and a data interface configured to communicate with a mating data interface of the second housing;
a tether attached to the first housing for retrieving the device; and
wherein the connected first housing is configured to be inserted in a vaginal tract;
inserting the retrievable device in the vaginal tract of the individual;
using the retrievable device to make at least one measurement of a first property of the individual;
using the tether to extract the retrievable device from the individual;
adding one or more sensors to the first housing;
reinserting the retrievable device in the vaginal tract of the individual; and
controlling the operation of the image capture device with a trigger signal generated based on the at least one measurement corresponding to a labor contraction.

16. The method of claim 15, further comprising the step of using the image capture device to capture at least one image of a portion of the cervical opening of the individual.

17. The method of claim 15, wherein the retrievable device further comprises a second housing having an analyte sensor, a mating connector configured to cooperate with the connector of the first housing for removable connection with the first housing, and a mating data interface configured to cooperate with the data interface of the first housing for communication with the first housing, and wherein the analyte sensor is used to make at least one measurement is of a concentration of an analyte in a vaginal fluid of the individual.

18. The method of claim 17, wherein the at least one measurement of analyte concentration is made continuously.

19. The method of claim 15, wherein the first housing further comprises a parametric sensor and the at least one measurement is of a physical parameter of an environment external to the device.

20. The method of claim 15, further comprising the step of transmitting the at least one measurement by way of a transmitter.

21. The method of claim 15, further comprising the step of receiving a control signal at the retrievable device from a remote transmitter.

22. The method of claim 15, further comprising the steps of:
configuring the retrievable device to make at least one measurement of a second property of the individual;
reinserting the retrievable device in the individual; and
using the reconfigured retrievable device to make at least one measurement of the second property of the individual.

* * * * *